(12) United States Patent
Li

(10) Patent No.: US 6,380,184 B1
(45) Date of Patent: Apr. 30, 2002

(54) BENZOAZEPINES AND ANALOGS THEREOF USEFUL AS GROWTH HORMONE SECRETAGOGUES

(75) Inventor: James J. Li, Pennington, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/417,180

(22) Filed: Oct. 12, 1999

Related U.S. Application Data

(60) Provisional application No. 60/105,969, filed on Oct. 28, 1998.

(51) Int. Cl.$^7$ .............. C07D 223/14; C07D 223/16; A61K 31/55; A61P 3/04; A61P 3/00
(52) U.S. Cl. .............. 514/213.01; 514/217; 540/586; 540/593
(58) Field of Search .............. 540/586, 593; 514/217, 213.01

(56) References Cited

U.S. PATENT DOCUMENTS

| | | | |
|---|---|---|---|
| 3,239,345 A | 3/1966 | Hodge et al. | 99/2 |
| 4,036,979 A | 7/1977 | Asato | 424/275 |
| 4,411,890 A | 10/1983 | Momany | 424/177 |
| 5,206,235 A | 4/1993 | Fisher et al. | 514/213 |
| 5,258,510 A * | 11/1993 | Ogawa et al. | 540/476 |
| 5,283,241 A | 2/1994 | Bochis et al. | 514/183 |
| 5,284,841 A | 2/1994 | Chu et al. | 514/183 |
| 5,310,737 A | 5/1994 | Fisher et al. | 514/215 |
| 5,317,017 A | 5/1994 | Ok et al. | 514/211 |
| 5,374,721 A | 12/1994 | Schoen et al. | 540/491 |
| 5,430,144 A | 7/1995 | Schoen et al. | 540/461 |
| 5,434,261 A | 7/1995 | Schoen et al. | 540/461 |
| 5,438,136 A | 8/1995 | Devita et al. | 540/456 |
| 5,536,716 A | 7/1996 | Chen et al. | 514/215 |
| 5,545,735 A | 8/1996 | Bochis et al. | 540/490 |
| 5,578,593 A | 11/1996 | Chen et al. | 514/212 |
| 5,583,130 A | 12/1996 | Bochis et al. | 514/183 |
| 5,606,054 A | 2/1997 | Fisher et al. | 540/521 |
| 5,622,973 A | 4/1997 | Morriello et al. | 514/318 |
| 5,652,235 A | 7/1997 | Chen et al. | 514/215 |
| 5,663,171 A | 9/1997 | Chen et al. | 514/19 |
| 5,672,596 A | 9/1997 | Wyvratt et al. | 514/183 |
| 5,726,307 A | 3/1998 | Schoen et al. | 540/491 |

FOREIGN PATENT DOCUMENTS

| | | |
|---|---|---|
| WO | WO 94/19367 | 9/1994 |
| WO | WO 95/16675 | 6/1995 |
| WO | WO 96/05195 | 2/1996 |
| WO | WO 96/22997 | 8/1996 |
| WO | WO 97/24369 | 7/1997 |
| WO | WO 98/58948 | 12/1998 |

OTHER PUBLICATIONS

CAS printout for WO 94/01113, Jan. 1994.*
CAS printout for WO 91/05549, May 1991.*
Bennett et al.,, (Ed.), Cecil Texbook of Medicine, W. B. Saunders Company, p. 1277, 1996.*

* cited by examiner

Primary Examiner—Brenda Coleman
(74) Attorney, Agent, or Firm—Burton Rodney; Ronald S. Hermenau

(57) ABSTRACT

Benzoazepines of the following formula wherein $R^1$, $R^{1a}$, $R^2$, $R^{9k}$, L, Q, X, Y and Z are as described herein, and analogs thereof are provided which are useful in stimulating endogenous production or release of growth hormone and in treating obesity, osteoporosis (improving bone density) and in improving muscle mass and muscle strength.

22 Claims, No Drawings

BENZOAZEPINES AND ANALOGS THEREOF USEFUL AS GROWTH HORMONE SECRETAGOGUES

This application claims priority to U.S. Provisional application Ser. No. 60/105,969 filed Oct. 28, 1998 the entirety of which is incorporated herein by reference.

FIELD OF THE INVENTION

The present invention relates to novel benzoazepines and analogs thereof which are growth hormone secretagogues, that is they stimulate endogenous production and/or release of growth hormone, and to methods for treating obesity and diabetes, improving bone density (to treat osteoporosis) and stimulating increase in muscle mass and muscle strength employing such compounds.

BACKGROUND OF THE INVENTION

The pituitary gland secretes growth hormone which stimulates growth in body tissue capable of growing and affects metabolic processes by increasing rate of protein synthesis and decreasing rate of carbohydrate synthesis in cells. Growth hormone also increases mobilization of free fatty acids and use of free fatty acids for energy.

The prior art is replete with patents/applications which disclose compounds which are useful as growth hormone secretagogues.

The following patents/applications, disclose benzofused lactams which are disclosed as being useful in promoting release of growth hormone:

U.S. Pat. Nos. 5,206,235; 5,283,741; 5,284,841; 5,310,737; 5,317,017; 5,374,721; 5,430,144; 5,434,261; 5,438,136; 5,545,735; 5,583,130; 5,606,054; 5,672,596 and 5,726,307; WO 96-05195 and WO 95-16675.

SUMMARY OF THE INVENTION

In accordance with the present invention, novel benzoazepines and analogs thereof are provided which are growth hormone secretagogues and have the structure

I

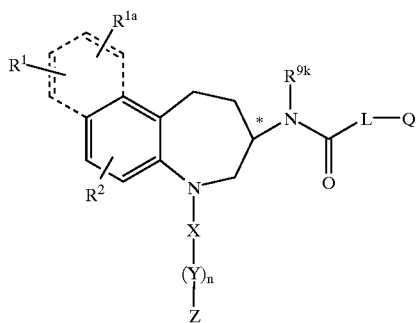

including pharmaceutically acceptable salts thereof and all stereoisomers thereof, wherein X is $(CH_2)_m$ where m is an integer from 0 to 4, CO, SO or $SO_2$;

Y is

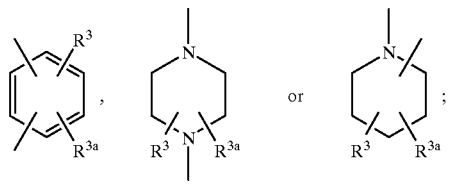

Z is

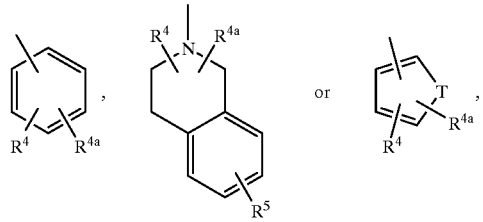

T is $N—R^6$, O or S;

provided that (1) where Y is

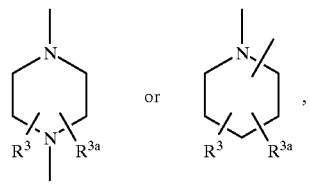

X is CO, SO or $SO_2$, or $(CH_2)_m$ where m is 2, 3 or 4, and (2) where Z is

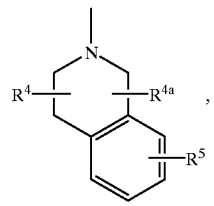

then n=o and X is CO, SO or $SO_2$ or $(CH_2)_m$ where m is 2, 3 or 4;

L is $—R^7—(CH_2)_q\text{-aryl-}(CH_2)_{q'}—$ or

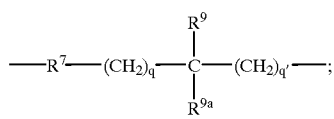

Q is $—NR^{10}R^{11}$,

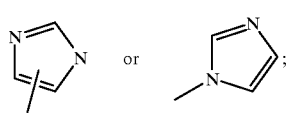

n is 0 to 1; p is 1 to 3; q is 0 to 3; q' is 0 to 3;

the benzene ring depicted by broken lines may or may not be fused to the benzo ring of the benzoazepine.

$R^1$, $R^{1a}$, $R^2$, $R^3$ and $R^4$ are independently selected from hydrogen, hydroxy, halogen, cyano, nitro, amino, $CF_3$, $OCF_3$, $S(O)_rR^{9b}$, $SO_2NR^{9b}R^{9c}$, $COOR^{9b}$, $CONR^{9b}R^{9c}$, $NR^{9b}COR^{9c}$, alkyl, cycloalkyl, alkoxyl, alkylaryl, acyl, aryl and heteroaryl where the alkyl, cycloalkyl, alkoxyl, alkylaryl, acyl, aryl and heteroaryl groups in $R^1$, $R^{1a}$, $R^2$, $R^3$ and $R^4$ are optionally substituted with hydroxy, halogen, cyano, nitro, amino, $CF_3$, $OCF_3$, $S(O)_rR^{9b}$, $SO_2NR^{9b}R^{9c}$, $CO_2R^{9b}$ or $CONR^{9b}R^{9c}$;

r is 0, 1 or 2;

$R^{3a}$, $R^{4a}$ and $R^5$ are independently selected from hydrogen, hydroxy, halogen, cyano, nitro, amino, $CF_3$, $OCF_3$, $CO_2H$, $CONH_2$, $SO_2NH_2$, $SO_2Me$, $NHCON(CH_3)_2$, $NHSO_2CH_3$, $NHSO_2N(CH_3)_2$, tetrazole, $R^{12}$alkyl, acyl, alkoxyl, alkylaryl, aryl or heteroaryl; $R^{12}$ is independently selected from a bond, oxygen, $CONR^{9d}$, $S(O)_t$, $SO_2NR^{9d}$, $NR^{9d}$, $NR^{9d}CO$, $NR^{9d}CONR^{9e}$, or $NR^{9d}SO_2$. The alkyl, acyl, alkoxyl, alkylaryl, aryl and heteroaryl groups in $R^{3a}$, $R^{4a}$ and $R^5$ can be optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_tR^{9f}$, $SO_2NR^{9f}R^{9g}$ or tetrazole; t and t' are independently from 0, 1 or 2.

$R^{12}$ is selected from a bond, oxygen, $CONR^{9d}$, $S(O)_t$, $SO_2NR^{9d}$, $NR^{9d}$, $NR^{9d}CO$, $NR^{9d}CONR^{9e}$, and $NR^{9d}SO_2$, and where alkyl, acyl, alkoxyl, alkylaryl, aryl and heteroaryl groups in $R^{3a}$, $R^{4a}$ and $R^5$ are optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_tR^{9f}$, $SO_2NR^{9f}R^{9g}$ or tetrazole;

t and t' are independently 0, 1 or 2;

$R^6$ is independently selected from hydrogen, $SO_2R^{9h}$, $SO_2NR^{9h}R^{9i}$, $CONR^{9h}R^{9i}$, alkyl, cycloalkyl, acyl or aryl where the alkyl, cycloalkyl, acyl or aryl groups in $R^6$ is optionally substituted with hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, or tetrazole;

$R^7$ is independently selected from a bond, oxygen or $NR^{9j}$;

$R^9$ and $R^{9a}$ are independently selected from hydrogen, $CF_3$, alkyl or alkylaryl, or $R^9$ and $R^{9a}$ can be joined together to form a 4 to 7 membered carbocyclic or heterocyclic ring, or either $R^9$ or $R^{9a}$, or both, can be joined with $R^{10}$ or $R^{11}$ to form a 4 to 7 membered heterocyclic ring; and $R^9$ and $R^{9a}$ can be optionally substituted with any of the substituents for $R^6$;

$R^{9b}$, $R^{9c}$, $R^{9d}$, $R^{9e}$, $R^{9f}$, $R^{9g}$, $R^{9h}$, $R^{9i}$, $R^{9j}$ and $R^{9k}$ are independently selected from hydrogen, $C_1-C_6$ alkyl or aryl;

$R^{10}$ and $R^{11}$ are independently selected from hydrogen, alkyl or alkylaryl where the alkyl and alkylaryl groups in $R^{10}$ and $R^{11}$ can be optionally substituted with 1, 2 or 3 of hydroxy, amino, alkoxyl, aryloxyl, acyl and imidazole; $R^{10}$ and $R^{11}$ can also be joined together to form a 4 to 7 membered heterocyclic ring.

Thus, the compounds of formula I of the invention preferably include compounds of the structure

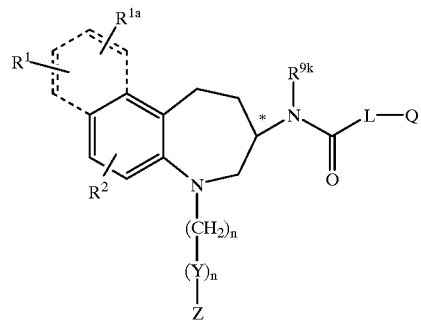

II

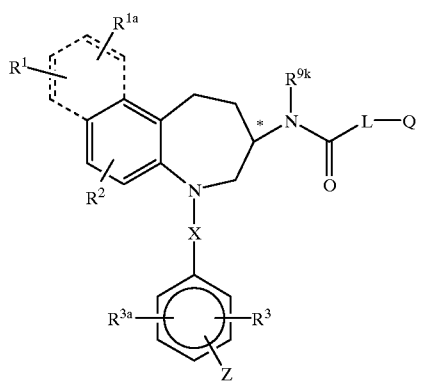

III

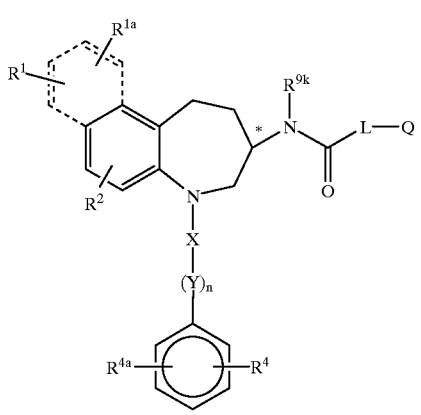

IV

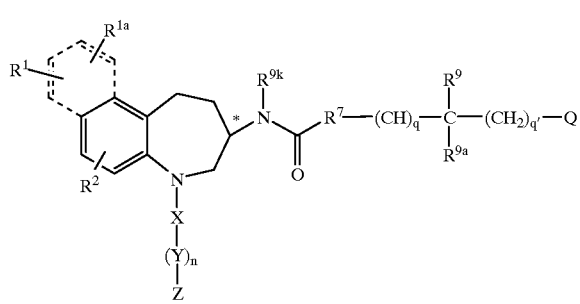

V

-continued

VI

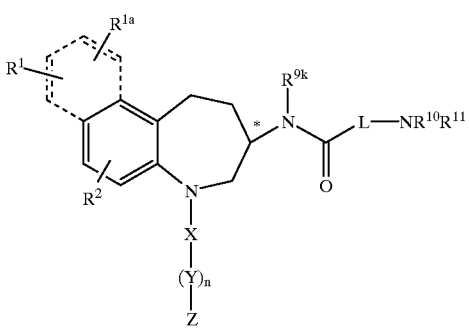

Most preferred are compounds of the structure VII

VII

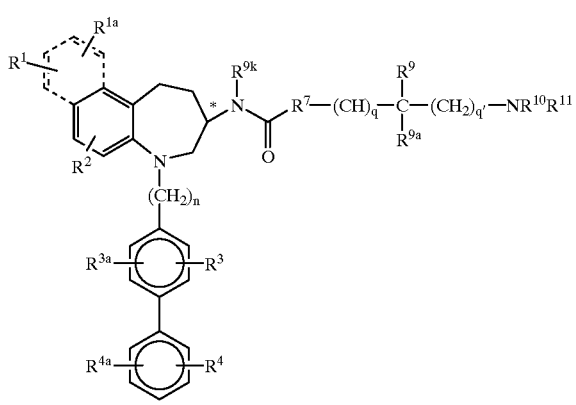

The compounds of the instant invention all have at least one asymmetric center as noted by the asterisk in structural formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in formula I, it has been found that the compound in which the 3-amino substituent is above the plane of the structure, as seen in formula I, is more active and thus more preferred over the compound in which the 3-amino substituent is below the plane of the structure. This center will be designated according to the R/S rules as R where the 3-amino substituent is above the plane.

The pharmaceutically acceptable salts of the compounds of formulae I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for increasing levels of endogenous growth hormone or increasing the endogenous production or release of growth hormone is provided wherein a compound of formula I as defined hereinbefore is administered in a therapeutically effective amount.

Furthermore, in accordance with the present invention, a method is provided for treating osteoporosis (improving bone density), or treating obesity, or treating diabetes, or increasing muscle mass and/or muscle strength, or renal disease, cardiac myopathy, cachexia, HIV wasting syndrome, long term critical illness (such as cancer), sarcopenia, and/or stimulating wound healing, immune system stimulation, and/or treating Syndrome X and/or Metabolic Syndrome, wherein a compound of formula I as defined hereinbefore is administered in a therapeutically effective amount.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents such as halogen, $CF_3$, haloalkyl, carbonyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino (wherein Ar is aryl or heteroaryl and Ar may optionally include 1, 2 or 3 additional rings fused to Ar), cycloalkylcarbonylamino, alkoxycarbonylamino, aryloxycarbonylamino, heteroaryloxycarbonylamino, uriedo (where the uriedo nitrogens may be substituted with alkyl, aryl or heteroaryl), heterocyclylcarbonylamino (where the heterocycle is heteroaryl or cycloheteroalkyl and is connected to the carbonyl group via a nitrogen or carbon atom), alkylsulfonylamino, arylsulfonylamino, heteroarylsulfonylamino, as well as any of the substituents as defined above for aryl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, cyclohexenyl,

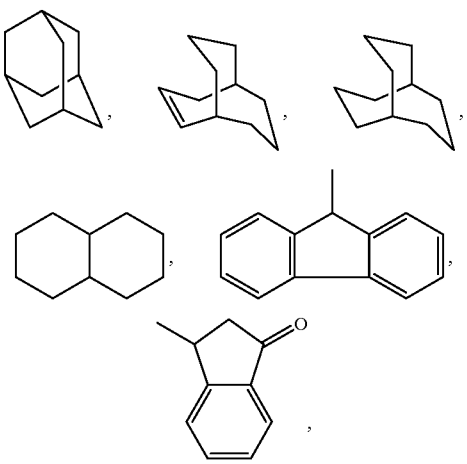

any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through available carbon atoms with 1, 2, or 3 groups selected from hydrogen, halo, haloalkyl, alkyl, alkoxy, haloalkoxy, alkenyl., trifluoromethyl, trifluoromethoxy, alkynyl, cycloalkylalkyl, cycloheteroalkyl, cycloheteroalkylalkyl, cycloheteroalkylcarbonyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, heteroarylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or preferably any of the aryl substituents as set out above.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxyl", "alkoxyl", "aryloxyl" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 2 to 6 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the substituents for alkyl as set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl as set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Examples of $(CH_2)_m$, $(CH_2)_q$ or $(CH_2)_{q'}$ groups (which may include alkylene, alkenylene or alkynylene groups as defined herein, and may optionally include 1, 2, or 3 substituents which may be any of the alkyl substituents set out herein), are as follows:

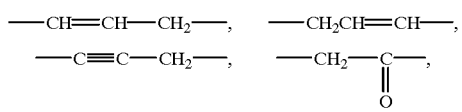

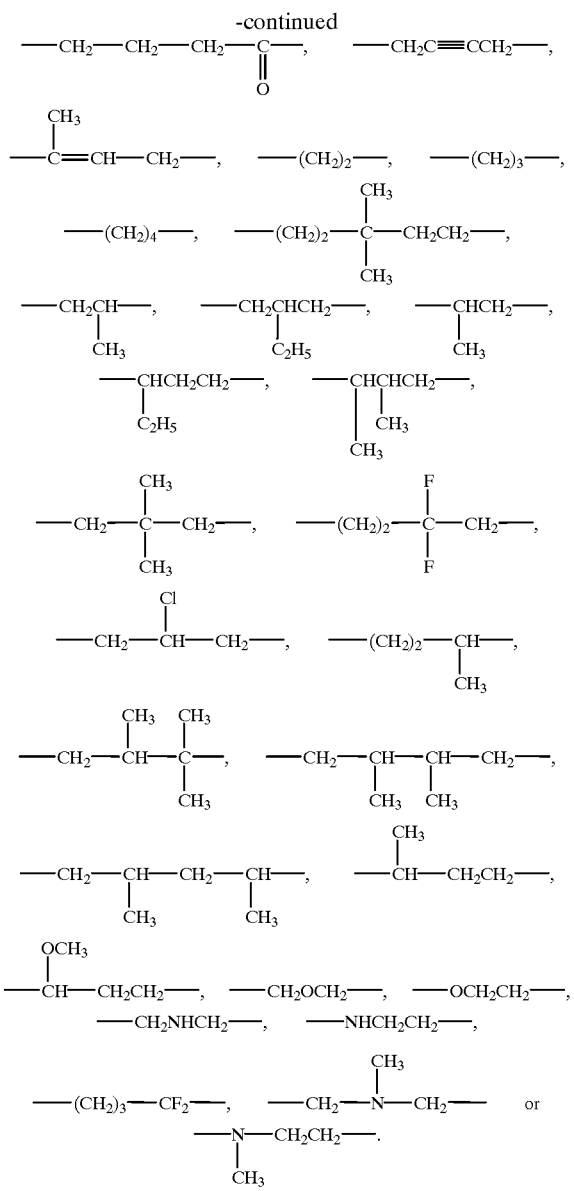

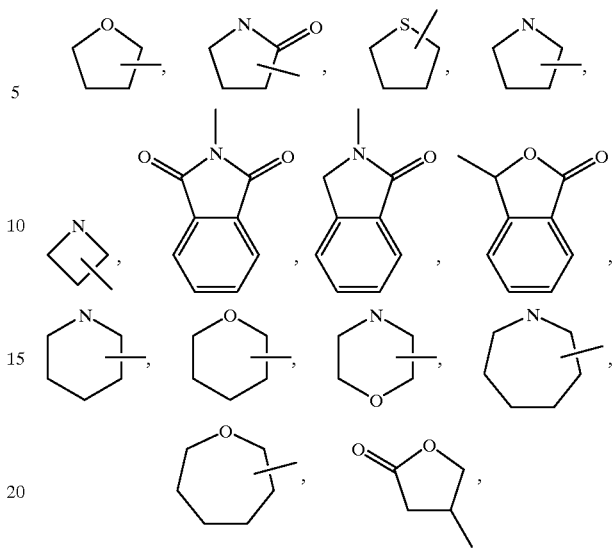

and the like. The above groups may include 1 to 4 substituents such as alkyl, halo, oxo and/or any of of the aryl substituents set out herein. In addition, any of the above rings can be fused to a cycloalkyl, aryl, heteroaryl or cycloheteroalkyl ring.

The term "cycloheteroalkoxy" as used herein alone or as part of another group refers to a 4-, 5-, 6- or 7-membered saturated or partially saturated ring which includes at least one oxygen atom in the ring and at least 1 or 2 other hetero atoms in the ring such as nitrogen, oxygen and/or sulfur, linked through a carbon or heteroatom, where possible, optionally via the linker $(CH_2)_p$, and which may include 1 to 4 substituents such as alkyl, halo, oxo and/or any of the aryl substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides, such as

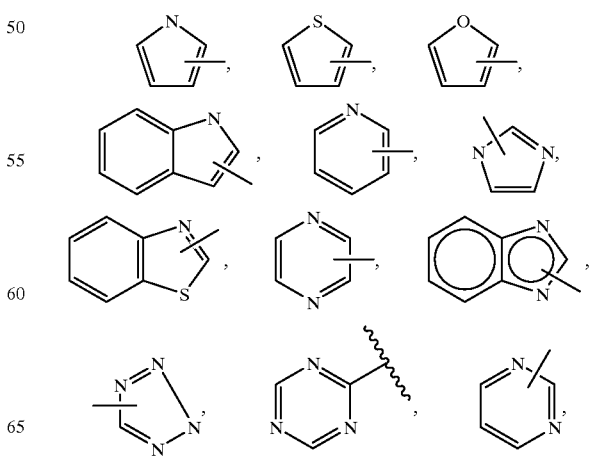

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclic", "heterocyclo" or "heterocycle" as employed herein alone or as part of another group refers to "heteroaryl" groups or "cycloheteroalkyl" groups.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

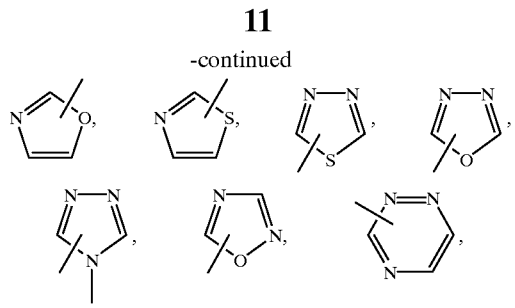

and the like.

The heteroaryl groups may optionally include 1 to 4 substituents such as any of the aryl substituents set out herein as well as carbonyl and arylcarbonyl. In addition, any of the above rings can be fused to a cycloalkyl, aryl, heteroaryl or cycloheteroalkyl ring.

General Synthetic Schemes

The compounds of the present invention may be prepared according to the following general synthetic schemes, as well as relevant published literature procedures that are used by the one skilled in the art. Exemplary reagents and procedures for these reactions appear hereinafter and in the working Examples. Unless otherwise specified, the various substituents of the compounds are defined in the same manner as the formula I compound of the invention.

The group Ar in Schemes II to VII and IX to XII is defined as

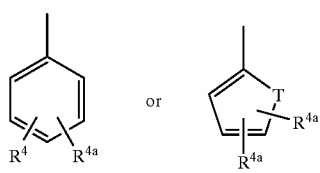

Scheme I

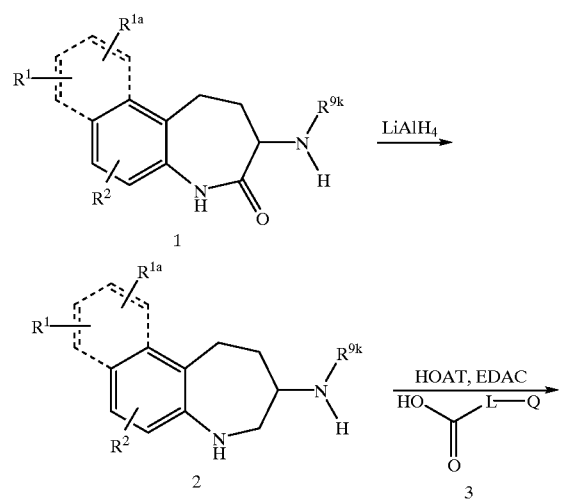

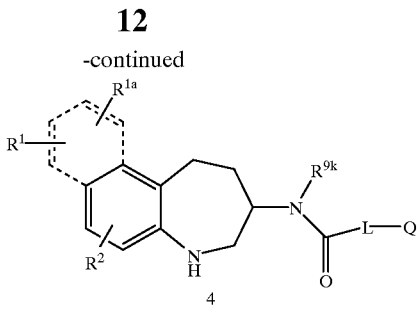

Synthetic Scheme I shows the preparation of intermediate 4.

The preparation of compound 1 is described by (1) Fisher, et al. U.S. Pat. No. 5,206,235; (2) T. R. Nieduzak et al. *Synth. Commun.* 26, 3443–3452 (1996) and (3) J. D. Armstrong, III et al. *Tetrahedron Lett.* 35, 3239–3242 (1994). Reduction of the amide carbonyl group in 1 is carried out with LAH in THF to give compound 2; subsequent reaction of compound 2 with carboxylic acid 3 in the presence of 1-ethyl-3-(3-dimethylaminopropyl)carbodiimide (EDAC) and 1-hydroxy-7-azabenzotriazole (HOAT) give intermediate compound 4.

Scheme II

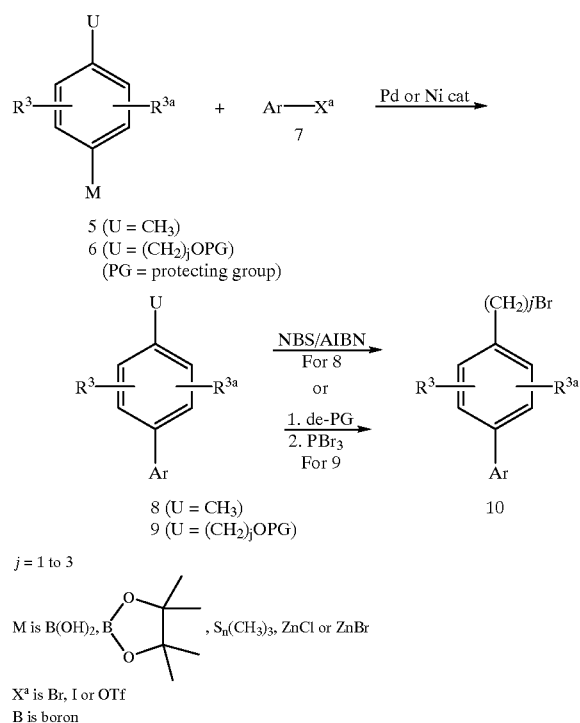

$j = 1$ to 3

M is $B(OH)_2$, B(pinacol), $Sn(CH_3)_3$, ZnCl or ZnBr $X^a$ is Br, I or OTf
B is boron Synthetic Scheme II shows the preparation of starting compound 10.

The preparation of intermediate compounds 5 and 6 is carried out according to (1) N. Miyaura et al. *Chem. Rev.* 95, 2457–2483 (1995), (2) T. Ishiyama et al. *J. Org. Chem.* 60, 7508–7510 (1995), (3) Minato et al. *Tetrahedron Lett.* 21, 845–848 (1980) and Mitchell et al. *Synthesis* 803–815 (1992). Aryl-aryl coupling reactions of 5 or 6 with 7 are mediated by a palladium or nickel catalyst to give the corresponding compound 8 or 9. Bromination of 8 with N-bromosuccinimide (NBS) in the presence of a radical initiator such as 2,2′-azobisisobutyronitrile (AIBN) gives compound 10. Alternatively, removal of the protecting group PG in 9 followed by the bromination with PBr₃ gives compound 10.

Scheme III

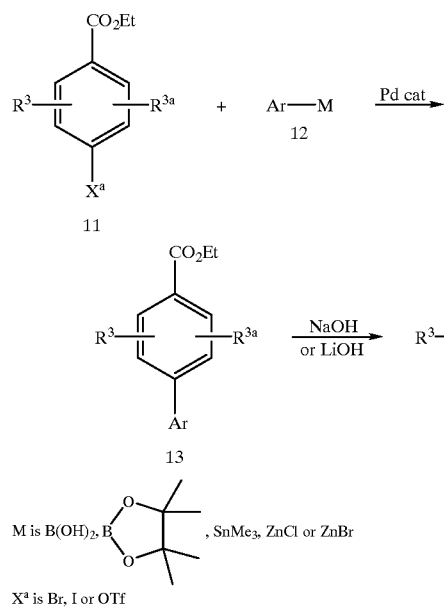

Synthetic Scheme III shows the preparation of starting compound 14. The preparation of intermediate compound 12 is carried out according to the same procedure as that of 5 or 6 (above). Aryl-aryl coupling reactions of 11 and 12 are mediated by a palladium or nickel catalyst 10 to give compound 13. Hydrolysis of the ethyl ester in 13 using NaOH or LiOH gives the compound 14.

Scheme IV

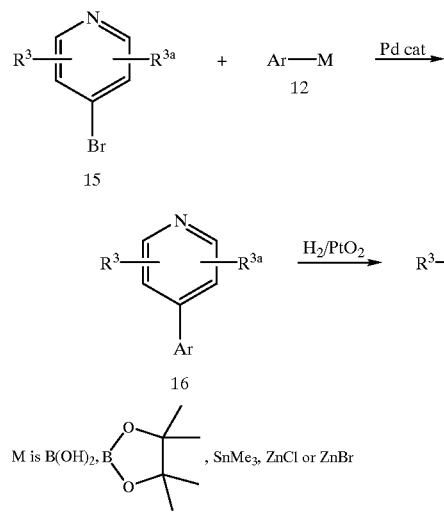

Synthetic Scheme IV shows the preparation of starting compound 17.

The preparation of intermediate compound 12 may be carried out according to the same procedure as that of 5 or 6 (above). Aryl-aryl coupling reactions of 12 and 15 are mediated by a palladium or nickel catalyst to give compound 16. Hydrogenation of pyridine ring in 16 is carried out in acetic acid with Pt₂O as the catalyst to give compound 17.

Synthetic Scheme V shows the preparation of starting compound 20.

The N-arylation of 19 is carried out in the presence of NaOt-Bu and a palladium catalyst to give compound 20.

Scheme V

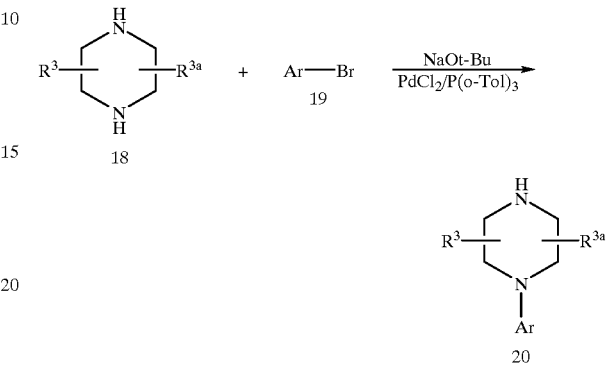

Synthetic Scheme VI shows the preparation of starting compounds 21–23.

Scheme VI

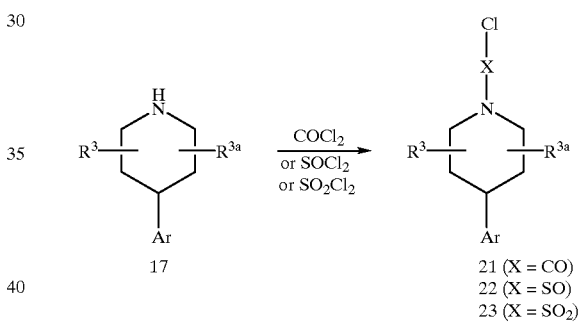

Reaction of 17 with COCl₂, SOCl₂ or SO₂Cl₂ gives the corresponding carbamyl chloride 21, sulfinyl chloride 22, or sulfonyl chloride 23.

Synthetic Scheme VII shows the preparation of starting compounds 24–26.

Scheme VII

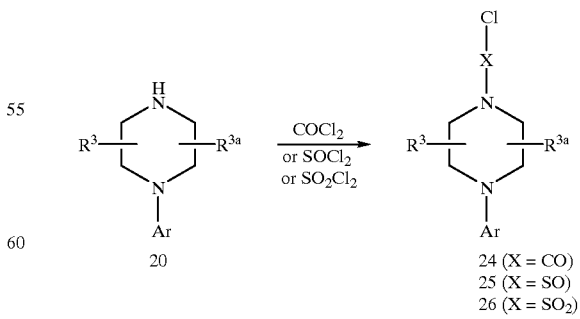

Reaction of 20 with COCl₂, SOCl₂ or SO₂Cl₂ gives the corresponding carbamyl chloride 24, sulfinyl chloride 25 or sulfonyl chloride 26.

Synthetic Scheme VIII shows the preparation of compounds of formula 28–30. Reaction of 27 with COCl$_2$, SOCl$_2$ or SO$_2$Cl$_2$ gives the corresponding carbamyl chloride 28, sulfinyl chloride 29 or sulfonyl chloride 30.

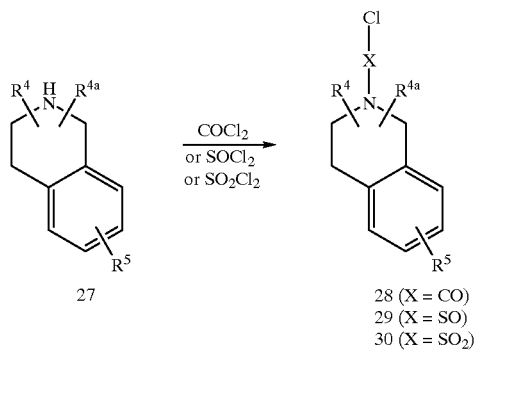

Synthetic Scheme IX shows the preparation of compound VIII of the invention.

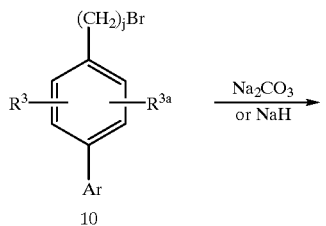

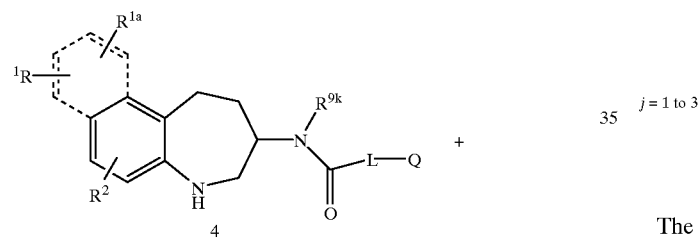

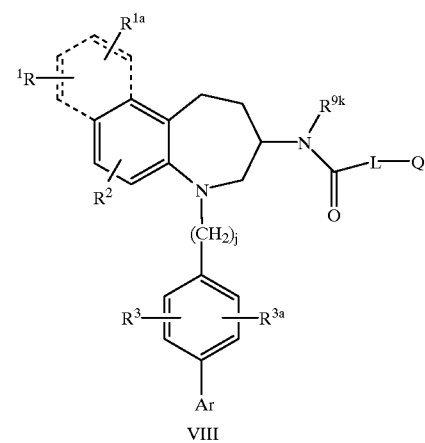

$j = 1$ to 3

The alkylation of compound 4 with 10 using a base such as Na$_2$CO$_3$ or NaH give the compound VIII of the invention.

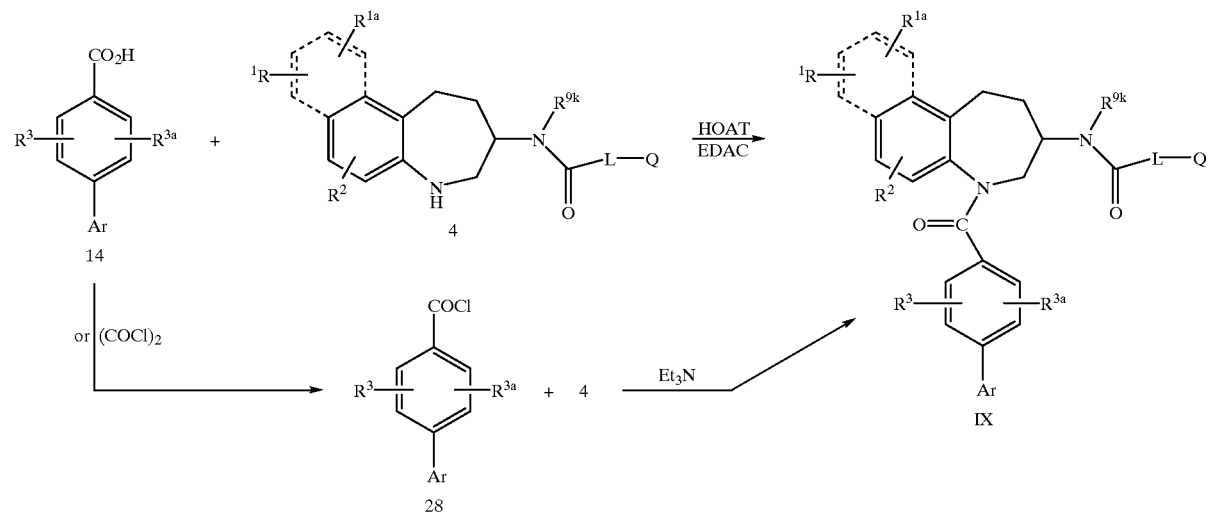

Synthetic Scheme X shows the preparation of compound IX of the invention. Reaction of 4 with a carboxylic acid 14 in the presence of EDAC and HOAT gives compound IX of the invention. Alternatively, compound 14 can be converted to acid chloride 28 with (COCl)$_2$; subsequent reaction with 4 in the presence of a base, such as Et$_3$N, give the compound IX of the invention.

Scheme XI

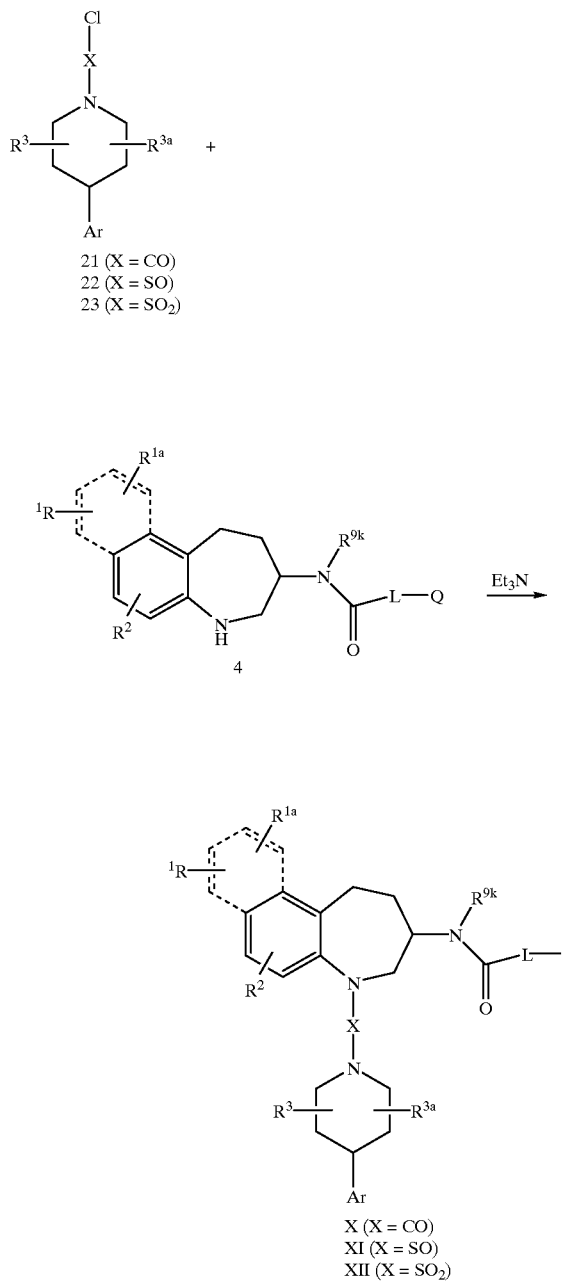

Synthetic Scheme XI shows the preparation of compounds of the invention X, XI and XII.

Reaction of 4 with 21, 22 or 23 in the presence of a base, such as Et$_3$N, gives the corresponding urea X of the invention, sulfinyl urea XI of the invention or sulfonyl urea XII of the invention.

Scheme XII

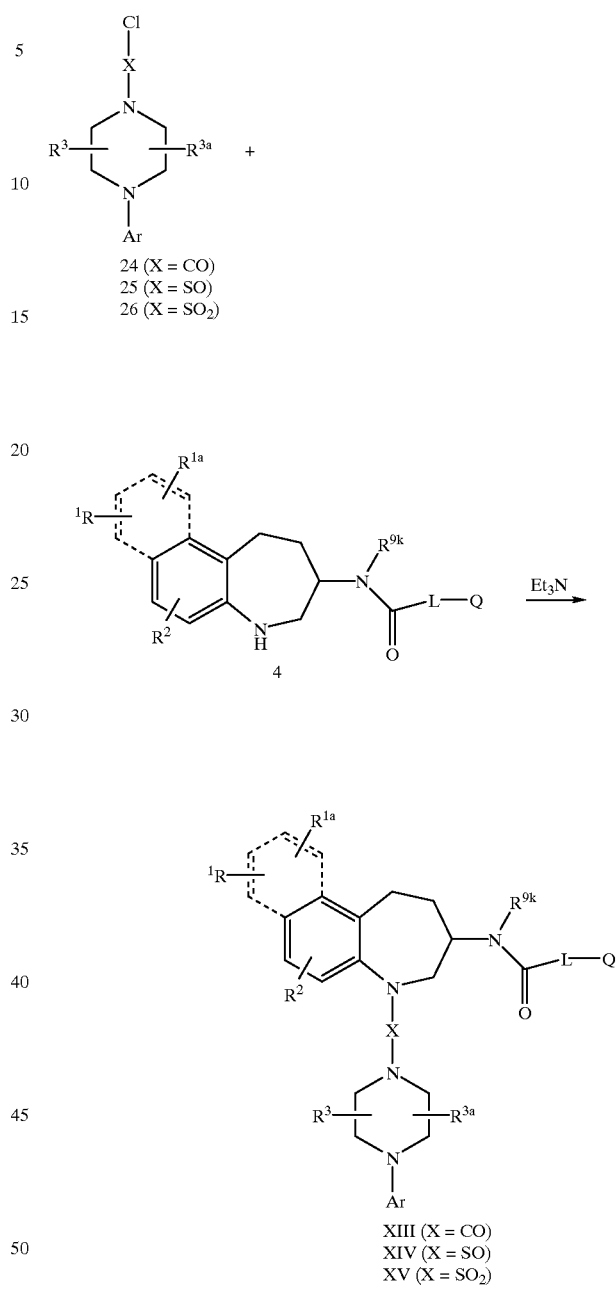

Synthetic Scheme XII shows the preparation of compounds of the invention XIII, XIV and XV. Reactions of 4 with 24, 25 or 26 in the presence of a base, such as Et$_3$N, gives the corresponding urea compound XIII of the invention, sulfinyl urea compound XIV of the invention or sulfonyl urea compound XV of the invention.

Synthetic Scheme XIII shows the preparation of compounds of the invention XIII, XIV or XV. Reactions of 4 with 28, 29 or 30 in the presence of a base, such as Et$_3$N, give the corresponding urea XVI, sulfinyl urea XVII or sulfonyl urea XVIII.

Scheme XIII

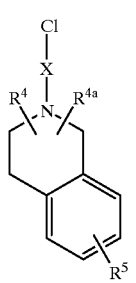

28 (X = CO)
29 (X = SO)
30 (X = SO$_2$)

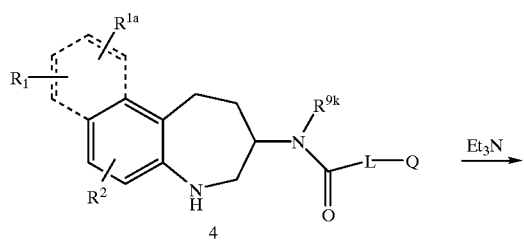

$\xrightarrow{\text{Et}_3\text{N}}$

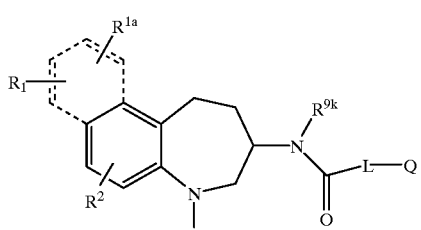

XVI (X = CO)
XVII (X = SO)
XVIII (X = SO$_2$)

Scheme XIV

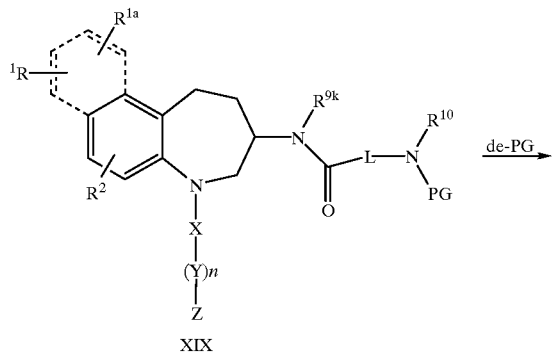

$\xrightarrow{\text{de-PG}}$

XIX

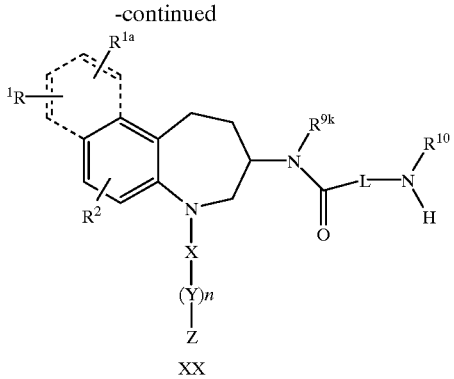

XX

Synthetic Scheme XIV describes preparation of compounds of the invention where Q is

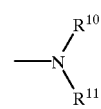

where $R^{11}$ in compound I is replaced by a protecting groups (PG) (compound XIX of the invention), and deprotection of XIX gives compound XX of the invention. In the cases where Boc is used as the protecting group, removal of the Boc group can be carried out with a strong acid such as trifluoroacetic acid (TFA) or HCl. In the cases where the Cbz group is used as the protecting group, it can be removed by catalytic hydrogenolysis or HBr in acetic acid. In the cases where other protecting groups may be used, removal conditions may be found in "Protective Groups in Organic Synthesis", Greene, et al. John Wiley and Sons Inc, 1991 or other known methods in the art.

Scheme XV

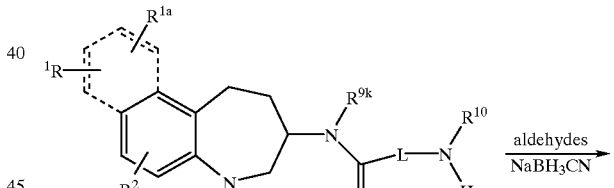

$\xrightarrow[\text{NaBH}_3\text{CN}]{\text{aldehydes}}$

XXI

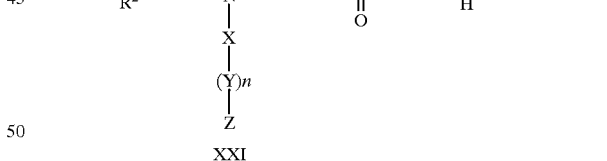

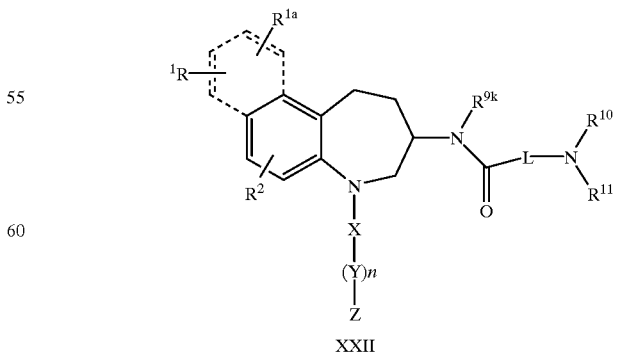

XXII

Synthetic Scheme XV describes further elaboration of compound XXI of the invention. Reductive amination of XXI with an aldehyde in the presence of reducing agent such as NaBH$_3$CN gives compound XXII of the invention.

The conditions described here for carrying out each step in the general synthetic schemes are conventional and capable of wide variation. They are presented for illustrative purpose only and are not intended as a restriction on the scope of invention.

Final compounds can be easily purified by recrystallization, silica gel chromatography, or reverse phase prep HPLC. In the cases where reverse phase prep HPLC is used, a mixture of solvent A (10% MeOH/90% H$_2$O/0.2% TFA) and solvent B (90% MeOH/10% H$_2$O/0.2% TFA) are used.

Most preferred are compounds of formula I of the invention having the structure

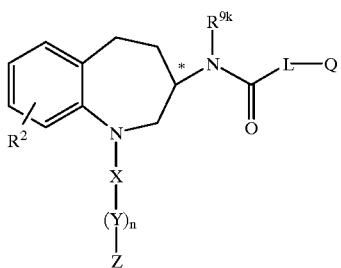

wherein R$^2$ is H;

X is (CH$_2$)$_m$ where m is 1;

Y is

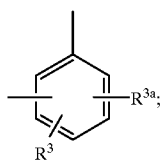

where R$^3$ and R$^{3a}$ are preferably H, and n is 1;

Z is

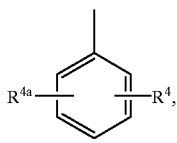

where R$^4$ is 2-tetrazole;

R$^{9k}$ is H;

L is

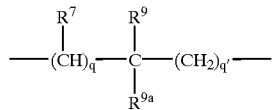

where q is 0 or 1; R$^7$ is H, R$^9$ and R$^{9a}$ are alkyl, preferably methyl;

Q is —NR$^{10}$R$^{11}$ where one of R$^{10}$ and R$^{11}$ is H and the other is alkyl which includes a hydroxy substituent, such as 2-OH-propyl.

The compounds of formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed compounds of formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of formula I of the invention is in combination with parathyroid hormone or bisphosphonates, such as MK-217 (alendronate), in the treatment of osteoporosis or in combination with estrogen, testosterone, or a selective estrogen receptor modulator, such as tamoxifen or raloxifene, for the treatment of aspects of Metabolic Syndrome.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids, treatment of osteoporosis, stimulation and increase in muscle mass and muscle strength, stimulation of the immune system, treatment of growth retardation, acceleration of wound healing, acceleration of bone fracture repair, treatment of renal failure or insufficiency resulting in growth retardation, treatment of physiological short stature, including growth hormone deficient children, treatment of short stature associated with chronic illness, treatment of obesity and growth retardation associated with obesity, treating growth retardation associated with Prader-Willis syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS; treatment of hyperinsulinemia including nesidioblastosis; adjuvant treatment for ovulation induction; to stimulate thymic development and prevent the age-related decline of thymic function; treatment of immunosuppressed patients; improvement in muscle mobility, maintenance of skin thickness, metabolic homeostasis, diabetes (Type 2), improvement of body composition (by increasing lean body mass), and/or renal homeostasis in the frail elderly; stimulation of osteoblasts, bone remodeling, and cartilage growth; stimulation of the immune system in companion animals and treatment of disorders of aging in companion animals; growth promotant in livestock; and stimulation of wool growth in sheep and milk production in cows.

The above conditions, diseases and maladies which may be treated employing the compounds of the invention are collectively referenced to as "Syndrome X" or Metabolic Syndrome, as detailed in Johannsson, J. Clin. Endocrinol. Metab., 82, 727–34 (1997).

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

The following Examples represent preferred embodiments of the invention. All temperatures are in ° C. unless indicated otherwise.

EXAMPLE 1

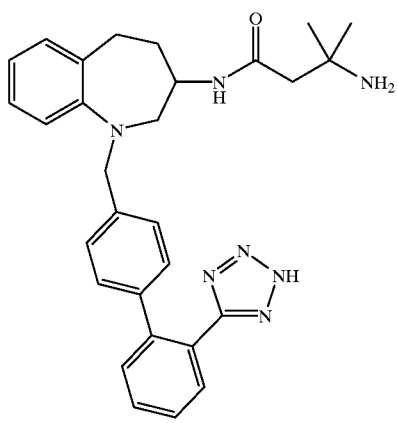

A.

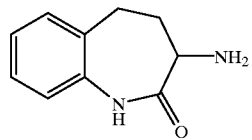

The intermediate A is prepared according to the published procedure, (1) T. R. Nieduzak et al. Commun. 1996, 26, 3443–3452 and (2) J. D. Armstrong, III et al. Tetrahedron Lett. 1994, 35, 3239–3242.

B.

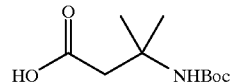

The intermediate B is prepared according to the published procedure, W. R. Schoen et al. J. Med. Chem. 1994, 37, 897–906.

C.

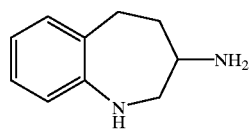

Under nitrogen, to a stirred solution of Part A intermediate (2.9 g, 16.5 mmol) in 100 mL of anhydrous THF was slowly added 33 mL of LAH (1.0 M in THF, 33.0 mmol) solution at −78° C. After the addition, the dry-ice bath was removed, and the reaction was allowed to warm to room temperature. It was refluxed for 50 hours, cooled down, then slowly quenched with aqueous THF. The inorganic salts were removed by filtration, and the solid was washed with THF several times. The liquid was concentrated, then dissolved in ethyl acetate, dried over Na$_2$SO$_4$ and concentrated in vacuo to give 1.9 g of title compound as yellow semi-solid. LC/MS m/z 163 (M+H)$^+$.

EXAMPLE 2

D.

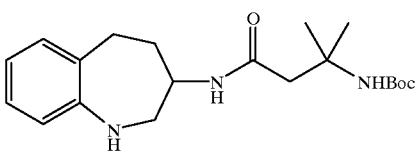

Under nitrogen, to a stirred solution of Part C compound (180 mg, 1.1 mmol) in 4 mL of CH$_2$Cl$_2$ were added Part B intermediate (220 mg, 1.0 mmol, Step 1), EDAC (230 mg, 1.2 mmol) and HOAT (165 mg, 1.2 mmol) at room temperature, and the stirring was continued overnight. The mixture was concentrated, then dissolved in ethyl acetate, washed with H$_2$O twice, dried over Na$_2$SO$_4$ and concentrated in vacuo. Purification on silica gel using 30% ethyl acetate/hexane gave 326 mg of title compound as a white solid. LC/MS m/z 362 (M+H)$^+$.

E.

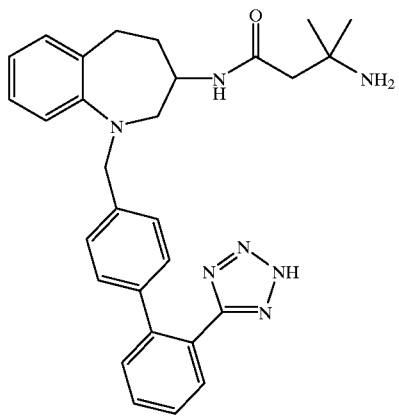

Under nitrogen, to a stirred solution of Part D compound (145 mg, 0.4 mmol) in 3 mL of dry acetone were added N-(triphenylmethyl)-5-[2-[4'-(bromomethyl)-biphenylyl]]-tetrazole (250 mg, 0.48 mmol, Bionet Ltd) and $K_2CO_3$ (166 mg, 1.2 mmol). The mixture was refluxed for 18 hours, cooled down, and concentrated. Ethyl acetate was then added, the ethyl acetate layer was washed with $H_2O$, dried over $Na_2SO_4$ and concentrated. Purification on silica gel using 25% ethyl acetate/hexane gave 120 mg of a white solid. To this solid was slowly added 3 mL of 4 N HCl/dioxane solution, and the mixture was stirred at room temperature for one hour. It was then concentrated, and purified on HPLC (25 to 100% solvent B) to give 60 mg of the title compound (as TFA salt) as pale yellow foam. LC/MS m/z 496 (M+H)$^+$.

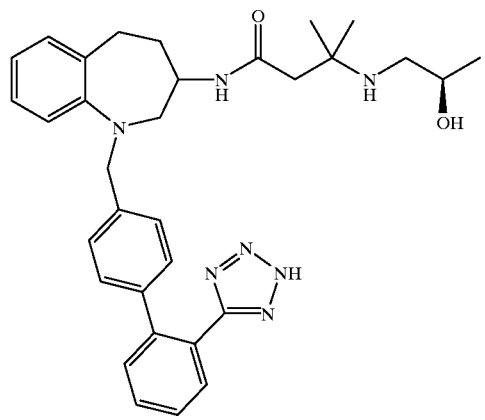

A.

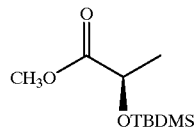

Under nitrogen, to a stirred solution of (R)-methyllactate (10 g, 96.1 mmol) in 100 mL of $CH_2Cl_2$ were added t-butyldimethylsilylchloride (TBDMSiCl) (17.4 g, 115.4 mmol) and imidazole (7.9 g, 116 mmol) at room temperature. A precipitate was formed, and the slurry was stirred at room temperature overnight. It was filtered through a pad of silica gel, and washed with $CH_2Cl_2$. The $CH_2Cl_2$ solution was concentrated to give 20.5 g of title compound as a colorless oil.

$^1$H NMR (400 MHz, CDCl$_3$) δ4.28 (q, J=7.0 Hz, 1H), 3.67 (s, 3H), 1.34 (d, J=7.0 Hz, 3H), 0.83 (s, 9H), 0.04 (s, 3H), 0.02 (s, 3H).

B.

Under nitrogen, to a stirred solution of Part A compound (2.8 g, 12.8 mmol, Step 1) in 30 mL of anhydrous THF was added 28.2 mL of diisobutylaluminum hydride (DIBAL-H) (1.0 M in THF, 28.2 mmol) solution at −78° C., and the stirring was continued at −78° C. for 3 hours. The reaction mixture was then slowly quenched with aqueous THF. The inorganic salts were removed by filtration, and washed with THF several times. The liquid was concentrated, then dissolved in ethyl acetate, dried over $Na_2SO_4$ and concentrated in vacuo to give 580 mg of title compound as an oil.

$^1$H NMR (400 MHz, CDCl$_3$) δ3.82–3.86 (m, 1H), 3.40–3.44 (m, 1H), 3.25–3.32 (m, 1H), 1.84–1.88 (m, 1H), 1.05 (d, J=6.2 Hz, 3H), 0.83 (s, 9H), 0.02 (s, 6H).

C.

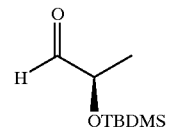

To a stirred solution of Part B compound (580 mg, 3.0 mmol) in 10 mL of $CH_2Cl_2$ was added pyridinium chlorochromate (PCC) (790 mg, 3.6 mmol), and the stirring was continued overnight at room temperature. The mixture was filtered through a silica gel pad, and concentrated. Purification on silica gel using hexane gave 120 mg of title compound as an oil.

$^1$H NMR (400 MHz, CDCl$_3$) δ9.56 (s, 1H), 4.05 (q, J=7.0 Hz, 1H), 1.22 (d, J=7.0 Hz, 3H), 0.87 (s, 9H), 0.05 (s, 3H), 0.04 (s, 3H).

D.

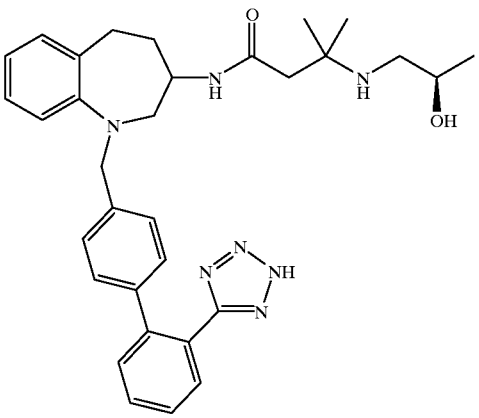

Under nitrogen, to a stirred solution of Example 1 compound (38 mg, 0.062 mmol) in 0.3 mL of dry methanol were added a solution of Part C compound (120 mg, 0.51 mmol) in 0.3 mL of dry methanol and 100 mg of molecular sieves. After the resulting slurry was stirred for 20 mins at room temperature, NaBH$_3$CN (25 mg, 0.4 mmol) was added, and the stirring was continued overnight at room temperature. The slurry was quenched with $H_2O$, filtered, and concentrated. The residue was dissolved in 2 mL of $Bu_4NF$ solution (1.0 M in THF), and stirred overnight at room temperature. It was concentrated, and purified on HPLC (30 to 100% solvent B) to give 16.8 mg of the title compound (as TFA salt) as pale yellow foam. LC/MS m/z 668 $(M+H)^+$.

Employing the procedures set out hereinbefore and in the working Examples, the following compounds of the present invention may be prepared.

TABLE 1

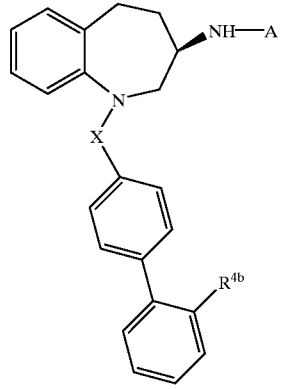

| $R^{4b}$ | X | A |
|---|---|---|
| CN | $CH_2$ | $COC(CH_3)_2NH_2$ |
| $CONH_2$ | $CH_2$ | $COC(CH_3)_2NH_2$ |
| $CH_2CONH_2$ | $CH_2$ | $COC(CH_3)_2NH_2$ |
| $(CH_2)_2CONH_2$ | $CH_2$ | $COC(CH_3)_2NH_2$ |
| $(CH_2)_3CONH_2$ | $CH_2$ | $COC(CH_3)_2NH_2$ |
| $(CH_2)_4CONH_2$ | $CH_2$ | $COC(CH_3)_2NH_2$ |
| $CONHC_2H_5$ | $CH_2$ | $COC(CH_3)_2NH_2$ |
| $CONH(CH_2)_3OH$ | $CH_2$ | $COC(CH_3)_2NH_2$ |
| $CONH(CH_2)_4OH$ | $CH_2$ | $COC(CH_3)_2NH_2$ |
| $CH_2CN_4H$ | $CH_2$ | $COC(CH_3)_2NH_2$ |
| $(CH_2)_2CN_4H$ | $CH_2$ | $COC(CH_3)_2NH_2$ |
| $(CH_2)_3CN_4H$ | $CH_2$ | $COC(CH_3)_2NH_2$ |
| $(CH_2)_4CN_4H$ | $CH_2$ | $COC(CH_3)_2NH_2$ |
| $CH_2NHCOCH_3$ | $CH_2$ | $COC(CH_3)_2NH_2$ |
| $CH_2NHCONH_2$ | $CH_2$ | $COC(CH_3)_2NH_2$ |
| $CH_2NHCONHCH_3$ | $CH_2$ | $COC(CH_3)_2NH_2$ |
| $CH_2NHCON(CH_3)_2$ | $CH_2$ | $COC(CH_3)_2NH_2$ |
| $CH_2NHCONHC_2H_5$ | $CH_2$ | $COC(CH_3)_2NH_2$ |
| $CH_2NHCONH(CH_2)_2CH_3$ | $CH_2$ | $COC(CH_3)_2NH_2$ |
| $CH_2NHCONH(CH_2)_2OH$ | $CH_2$ | $COC(CH_3)_2NH_2$ |
| $NHCONH_2$ | $CH_2$ | $COC(CH_3)_2NH_2$ |
| $NHCONHCH_3$ | $CH_2$ | $COC(CH_3)_2NH_2$ |
| $NHCONH(CH_2)_2OH$ | $CH_2$ | $COC(CH_3)_2NH_2$ |
| $NHSO_2NH_2$ | $CH_2$ | $COC(CH_3)_2NH_2$ |
| $NHSO_2NHCH_3$ | $CH_2$ | $COC(CH_3)_2NH_2$ |
| $NHSO_2N(CH_3)_2$ | $CH_2$ | $COC(CH_3)_2NH_2$ |
| $NHSO_2N(C_2H_5)_2$ | $CH_2$ | $COC(CH_3)_2NH_2$ |
| CN | CO | $COC(CH_3)_2NH_2$ |
| $CONH_2$ | CO | $COC(CH_3)_2NH_2$ |
| $CH_2CONH_2$ | CO | $COC(CH_3)_2NH_2$ |
| $(CH_2)_2CONH_2$ | CO | $COC(CH_3)_2NH_2$ |
| $(CH_2)_3CONH_2$ | CO | $COC(CH_3)_2NH_2$ |
| $(CH_2)_4CONH_2$ | CO | $COC(CH_3)_2NH_2$ |
| $CONHC_2H_5$ | CO | $COC(CH_3)_2NH_2$ |
| $CONH(CH_2)_3OH$ | CO | $COC(CH_3)_2NH_2$ |
| $CONH(CH_2)_4OH$ | CO | $COC(CH_3)_2NH_2$ |
| $CN_4H$ | CO | $COC(CH_3)_2NH_2$ |
| $CH_2CN_4H$ | CO | $COC(CH_3)_2NH_2$ |
| $(CH_2)_2CN_4H$ | CO | $COC(CH_3)_2NH_2$ |
| $(CH_2)_3CN_4H$ | CO | $COC(CH_3)_2NH_2$ |
| $(CH_2)_4CN_4H$ | CO | $COC(CH_3)_2NH_2$ |
| $CH_2NHCOCH_3$ | CO | $COC(CH_3)_2NH_2$ |
| $CH_2NHCONH_2$ | CO | $COC(CH_3)_2NH_2$ |
| $CH_2NHCONHCH_3$ | CO | $COC(CH_3)_2NH_2$ |
| $CH_2NHCON(CH_3)_2$ | CO | $COC(CH_3)_2NH_2$ |
| $CH_2NHCONHC_2H_5$ | CO | $COC(CH_3)_2NH_2$ |
| $CH_2NHCONH(CH_2)_2CH_3$ | CO | $COC(CH_3)_2NH_2$ |
| $CH_2NHCONH(CH_2)_2OH$ | CO | $COC(CH_3)_2NH_2$ |
| $NHCONH_2$ | CO | $COC(CH_3)_2NH_2$ |
| $NHCONHCH_3$ | CO | $COC(CH_3)_2NH_2$ |

TABLE 1-continued

| $R^{4b}$ | X | A |
|---|---|---|
| NHCONH(CH$_2$)$_2$OH | CO | COC(CH$_3$)$_2$NH$_2$ |
| NHSO$_2$NH$_2$ | CO | COC(CH$_3$)$_2$NH$_2$ |
| NHSO$_2$NHCH$_3$ | CO | COC(CH$_3$)$_2$NH$_2$ |
| NHSO$_2$N(CH$_3$)$_2$ | CO | COC(CH$_3$)$_2$NH$_2$ |
| NHSO$_2$N(C$_2$H$_5$)$_2$ | CO | COC(CH$_3$)$_2$NH$_2$ |
| CN | CH$_2$ | COCH$_2$C(CH$_3$)$_2$NH$_2$ |
| CONH$_2$ | CH$_2$ | COCH$_2$C(CH$_3$)$_2$NH$_2$ |
| CH$_2$CONH$_2$ | CH$_2$ | COCH$_2$C(CH$_3$)$_2$NH$_2$ |
| (CH$_2$)$_2$CONH$_2$ | CH$_2$ | COCH$_2$C(CH$_3$)$_2$NH$_2$ |
| (CH$_2$)$_3$CONH$_2$ | CH$_2$ | COCH$_2$C(CH$_3$)$_2$NH$_2$ |
| (CH$_2$)$_4$CONH$_2$ | CH$_2$ | COCH$_2$C(CH$_3$)$_2$NH$_2$ |
| CONHC$_2$H$_5$ | CH$_2$ | COCH$_2$C(CH$_3$)$_2$NH$_2$ |
| CONH(CH$_2$)$_3$OH | CH$_2$ | COCH$_2$C(CH$_3$)$_2$NH$_2$ |
| CONH(CH$_2$)$_4$OH | CH$_2$ | COCH$_2$C(CH$_3$)$_2$NH$_2$ |
| CH$_2$CN$_4$H | CH$_2$ | COCH$_2$C(CH$_3$)$_2$NH$_2$ |
| (CH$_2$)$_2$CN$_4$H | CH$_2$ | COCH$_2$C(CH$_3$)$_2$NH$_2$ |
| (CH$_2$)$_3$CN$_4$H | CH$_2$ | COCH$_2$C(CH$_3$)$_2$NH$_2$ |
| (CH$_2$)$_4$CN$_4$H | CH$_2$ | COCH$_2$C(CH$_3$)$_2$NH$_2$ |
| CH$_2$NHCOCH$_3$ | CH$_2$ | COCH$_2$C(CH$_3$)$_2$NH$_2$ |
| CH$_2$NHCONH$_2$ | CH$_2$ | COCH$_2$C(CH$_3$)$_2$NH$_2$ |
| CH$_2$NHCONHCH$_3$ | CH$_2$ | COCH$_2$C(CH$_3$)$_2$NH$_2$ |
| CH$_2$NHCON(CH$_3$)$_2$ | CH$_2$ | COCH$_2$C(CH$_3$)$_2$NH$_2$ |
| CH$_2$NHCONHC$_2$H$_5$ | CH$_2$ | COCH$_2$C(CH$_3$)$_2$NH$_2$ |
| CH$_2$NHCONH(CH$_2$)$_2$CH$_3$ | CH$_2$ | COCH$_2$C(CH$_3$)$_2$NH$_2$ |
| CH$_2$NHCONH(CH$_2$)$_2$OH | CH$_2$ | COCH$_2$C(CH$_3$)$_2$NH$_2$ |
| NHCONH$_2$ | CH$_2$ | COCH$_2$C(CH$_3$)$_2$NH$_2$ |
| NHCONHCH$_3$ | CH$_2$ | COCH$_2$C(CH$_3$)$_2$NH$_2$ |
| NHCONH(CH$_2$)$_2$OH | CH$_2$ | COCH$_2$C(CH$_3$)$_2$NH$_2$ |
| NHSO$_2$NH$_2$ | CH$_2$ | COCH$_2$C(CH$_3$)$_2$NH$_2$ |
| NHSO$_2$NHCH$_3$ | CH$_2$ | COCH$_2$C(CH$_3$)$_2$NH$_2$ |
| NHSO$_2$N(CH$_3$)$_2$ | CH$_2$ | COCH$_2$C(CH$_3$)$_2$NH$_2$ |
| NHSO$_2$N(C$_2$H$_5$)$_2$ | CH$_2$ | COCH$_2$C(CH$_3$)$_2$NH$_2$ |
| CN | CO | COCH$_2$C(CH$_3$)$_2$NH$_2$ |
| CONH$_2$ | CO | COCH$_2$C(CH$_3$)$_2$NH$_2$ |
| CH$_2$CONH$_2$ | CO | COCH$_2$C(CH$_3$)$_2$NH$_2$ |
| (CH$_2$)$_2$CONH$_2$ | CO | COCH$_2$C(CH$_3$)$_2$NH$_2$ |
| (CH$_2$)$_3$CONH$_2$ | CO | COCH$_2$C(CH$_3$)$_2$NH$_2$ |
| (CH$_2$)$_4$CONH$_2$ | CO | COCH$_2$C(CH$_3$)$_2$NH$_2$ |
| CONHC$_2$H$_5$ | CO | COCH$_2$C(CH$_3$)$_2$NH$_2$ |
| CONH(CH$_2$)$_3$OH | CO | COCH$_2$C(CH$_3$)$_2$NH$_2$ |
| CONH(CH$_2$)$_4$OH | CO | COCH$_2$C(CH$_3$)$_2$NH$_2$ |
| CH$_2$CN$_4$H | CO | COCH$_2$C(CH$_3$)$_2$NH$_2$ |
| (CH$_2$)$_2$CN$_4$H | CO | COCH$_2$C(CH$_3$)$_2$NH$_2$ |
| (CH$_2$)$_3$CN$_4$H | CO | COCH$_2$C(CH$_3$)$_2$NH$_2$ |
| (CH$_2$)$_4$CN$_4$H | CO | COCH$_2$C(CH$_3$)$_2$NH$_2$ |
| CH$_2$NHCOCH$_3$ | CO | COCH$_2$C(CH$_3$)$_2$NH$_2$ |
| CH$_2$NHCONH$_2$ | CO | COCH$_2$C(CH$_3$)$_2$NH$_2$ |
| CH$_2$NHCONHCH$_3$ | CO | COCH$_2$C(CH$_3$)$_2$NH$_2$ |
| CH$_2$NHCON(CH$_3$)$_2$ | CO | COCH$_2$C(CH$_3$)$_2$NH$_2$ |
| CH$_2$NHCONHC$_2$H$_5$ | CO | COCH$_2$C(CH$_3$)$_2$NH$_2$ |
| CH$_2$NHCONH(CH$_2$)$_2$CH$_3$ | CO | COCH$_2$C(CH$_3$)$_2$NH$_2$ |
| CH$_2$NHCONH(CH$_2$)$_2$OH | CO | COCH$_2$C(CH$_3$)$_2$NH$_2$ |
| NHCONH$_2$ | CO | COCH$_2$C(CH$_3$)$_2$NH$_2$ |
| NHCONHCH$_3$ | CO | COCH$_2$C(CH$_3$)$_2$NH$_2$ |
| NHCONH(CH$_2$)$_2$OH | CO | COCH$_2$C(CH$_3$)$_2$NH$_2$ |
| NHSO$_2$NH$_2$ | CO | COCH$_2$C(CH$_3$)$_2$NH$_2$ |
| NHSO$_2$NHCH$_3$ | CO | COCH$_2$C(CH$_3$)$_2$NH$_2$ |

TABLE 1-continued

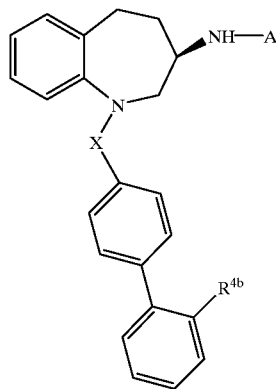

| R4b | X | A |
|---|---|---|
| NHSO$_2$N(CH$_3$)$_2$ | CO | COCH$_2$C(CH$_3$)$_2$NH$_2$ |
| NHSO$_2$N(C$_2$H$_5$)$_2$ | CO | COCH$_2$C(CH$_3$)$_2$NH$_2$ |
| CN | CH$_2$ | COCH$_2$C(CH$_3$)$_2$NHCH$_2$CH(OH)CH$_3$ |
| CONH$_2$ | CH$_2$ | COCH$_2$C(CH$_3$)$_2$NHCH$_2$CH(OH)CH$_3$ |
| CH$_2$CONH$_2$ | CH$_2$ | COCH$_2$C(CH$_3$)$_2$NHCH$_2$CH(OH)CH$_3$ |
| (CH$_2$)$_2$CONH$_2$ | CH$_2$ | COCH$_2$C(CH$_3$)$_2$NHCH$_2$CH(OH)CH$_3$ |
| (CH$_2$)$_3$CONH$_2$ | CH$_2$ | COCH$_2$C(CH$_3$)$_2$NHCH$_2$CH(OH)CH$_3$ |
| (CH$_2$)$_4$CONH$_2$ | CH$_2$ | COCH$_2$C(CH$_3$)$_2$NHCH$_2$CH(OH)CH$_3$ |
| CONHC$_2$H$_5$ | CH$_2$ | COCH$_2$C(CH$_3$)$_2$NHCH$_2$CH(OH)CH$_3$ |
| CONH(CH$_2$)$_3$OH | CH$_2$ | COCH$_2$C(CH$_3$)$_2$NHCH$_2$CH(OH)CH$_3$ |
| CONH(CH$_2$)$_4$OH | CH$_2$ | COCH$_2$C(CH$_3$)$_2$NHCH$_2$CH(OH)CH$_3$ |
| CH$_2$CN$_4$H | CH$_2$ | COCH$_2$C(CH$_3$)$_2$NHCH$_2$CH(OH)CH$_3$ |
| (CH$_2$)$_2$CN$_4$H | CH$_2$ | COCH$_2$C(CH$_3$)$_2$NHCH$_2$CH(OH)CH$_3$ |
| (CH$_2$)$_3$CN$_4$H | CH$_2$ | COCH$_2$C(CH$_3$)$_2$NHCH$_2$CH(OH)CH$_3$ |
| (CH$_2$)$_4$CN$_4$H | CH$_2$ | COCH$_2$C(CH$_3$)$_2$NHCH$_2$CH(OH)CH$_3$ |
| CH$_2$NHCOCH$_3$ | CH$_2$ | COCH$_2$C(CH$_3$)$_2$NHCH$_2$CH(OH)CH$_3$ |
| CH$_2$NHCONH$_2$ | CH$_2$ | COCH$_2$C(CH$_3$)$_2$NHCH$_2$CH(OH)CH$_3$ |
| CH$_2$NHCONHCH$_3$ | CH$_2$ | COCH$_2$C(CH$_3$)$_2$NHCH$_2$CH(OH)CH$_3$ |
| CH$_2$NHCON(CH$_3$)$_2$ | CH$_2$ | COCH$_2$C(CH$_3$)$_2$NHCH$_2$CH(OH)CH$_3$ |
| CH$_2$NHCONHC$_2$H$_5$ | CH$_2$ | COCH$_2$C(CH$_3$)$_2$NHCH$_2$CH(OH)CH$_3$ |
| CH$_2$NHCONH(CH$_2$)$_2$CH$_3$ | CH$_2$ | COCH$_2$C(CH$_3$)$_2$NHCH$_2$CH(OH)CH$_3$ |
| CH$_2$NHCONH(CH$_2$)$_2$OH | CH$_2$ | COCH$_2$C(CH$_3$)$_2$NHCH$_2$CH(OH)CH$_3$ |
| NHCONH$_2$ | CH$_2$ | COCH$_2$C(CH$_3$)$_2$NHCH$_2$CH(OH)CH$_3$ |
| NHCONHCH$_3$ | CH$_2$ | COCH$_2$C(CH$_3$)$_2$NHCH$_2$CH(OH)CH$_3$ |
| NHCONH(CH$_2$)$_2$OH | CH$_2$ | COCH$_2$C(CH$_3$)$_2$NHCH$_2$CH(OH)CH$_3$ |
| NHSO$_2$NH$_2$ | CH$_2$ | COCH$_2$C(CH$_3$)$_2$NHCH$_2$CH(OH)CH$_3$ |
| NHSO$_2$NHCH$_3$ | CH$_2$ | COCH$_2$C(CH$_3$)$_2$NHCH$_2$CH(OH)CH$_3$ |
| NHSO$_2$N(CH$_3$)$_2$ | CH$_2$ | COCH$_2$C(CH$_3$)$_2$NHCH$_2$CH(OH)CH$_3$ |
| NHSO$_2$N(C$_2$H$_5$)$_2$ | CH$_2$ | COCH$_2$C(CH$_3$)$_2$NHCH$_2$CH(OH)CH$_3$ |
| CN | CO | COCH$_2$C(CH$_3$)$_2$NHCH$_2$CH(OH)CH$_3$ |
| CONH$_2$ | CO | COCH$_2$C(CH$_3$)$_2$NHCH$_2$CH(OH)CH$_3$ |
| CH$_2$CONH$_2$ | CO | COCH$_2$C(CH$_3$)$_2$NHCH$_2$CH(OH)CH$_3$ |
| (CH$_2$)$_2$CONH$_2$ | CO | COCH$_2$C(CH$_3$)$_2$NHCH$_2$CH(OH)CH$_3$ |
| (CH$_2$)$_3$CONH$_2$ | CO | COCH$_2$C(CH$_3$)$_2$NHCH$_2$CH(OH)CH$_3$ |
| (CH$_2$)$_4$CONH$_2$ | CO | COCH$_2$C(CH$_3$)$_2$NHCH$_2$CH(OH)CH$_3$ |
| CONHC$_2$H$_5$ | CO | COCH$_2$C(CH$_3$)$_2$NHCH$_2$CH(OH)CH$_3$ |
| CONH(CH$_2$)$_3$OH | CO | COCH$_2$C(CH$_3$)$_2$NHCH$_2$CH(OH)CH$_3$ |
| CONH(CH$_2$)$_4$OH | CO | COCH$_2$C(CH$_3$)$_2$NHCH$_2$CH(OH)CH$_3$ |
| CN$_4$H | CO | COCH$_2$C(CH$_3$)$_2$NHCH$_2$CH(OH)CH$_3$ |
| CH$_2$CN$_4$H | CO | COCH$_2$C(CH$_3$)$_2$NHCH$_2$CH(OH)CH$_3$ |
| (CH$_2$)$_2$CN$_4$H | CO | COCH$_2$C(CH$_3$)$_2$NHCH$_2$CH(OH)CH$_3$ |
| (CH$_2$)$_3$CN$_4$H | CO | COCH$_2$C(CH$_3$)$_2$NHCH$_2$CH(OH)CH$_3$ |
| (CH$_2$)$_4$CN$_4$H | CO | COCH$_2$C(CH$_3$)$_2$NHCH$_2$CH(OH)CH$_3$ |
| CH$_2$NHCOCH$_3$ | CO | COCH$_2$C(CH$_3$)$_2$NHCH$_2$CH(OH)CH$_3$ |
| CH$_2$NHCONH$_2$ | CO | COCH$_2$C(CH$_3$)$_2$NHCH$_2$CH(OH)CH$_3$ |
| CH$_2$NHCONHCH$_3$ | CO | COCH$_2$C(CH$_3$)$_2$NHCH$_2$CH(OH)CH$_3$ |
| CH$_2$NHCON(CH$_3$)$_2$ | CO | COCH$_2$C(CH$_3$)$_2$NHCH$_2$CH(OH)CH$_3$ |
| CH$_2$NHCONHC$_2$H$_5$ | CO | COCH$_2$C(CH$_3$)$_2$NHCH$_2$CH(OH)CH$_3$ |
| CH$_2$NHCONH(CH$_2$)$_2$CH$_3$ | CO | COCH$_2$C(CH$_3$)$_2$NHCH$_2$CH(OH)CH$_3$ |
| CH$_2$NHCONH(CH$_2$)$_2$OH | CO | COCH$_2$C(CH$_3$)$_2$NHCH$_2$CH(OH)CH$_3$ |
| NHCONH$_2$ | CO | COCH$_2$C(CH$_3$)$_2$NHCH$_2$CH(OH)CH$_3$ |
| NHCONHCH$_3$ | CO | COCH$_2$C(CH$_3$)$_2$NHCH$_2$CH(OH)CH$_3$ |
| NHCONH(CH$_2$)$_2$OH | CO | COCH$_2$C(CH$_3$)$_2$NHCH$_2$CH(OH)CH$_3$ |
| NHSO$_2$NH$_2$ | CO | COCH$_2$C(CH$_3$)$_2$NHCH$_2$CH(OH)CH$_3$ |
| NHSO$_2$NHCH$_3$ | CO | COCH$_2$C(CH$_3$)$_2$NHCH$_2$CH(OH)CH$_3$ |
| NHSO$_2$N(CH$_3$)$_2$ | CO | COCH$_2$C(CH$_3$)$_2$NHCH$_2$CH(OH)CH$_3$ |
| NHSO$_2$N(C$_2$H$_5$)$_2$ | CO | COCH$_2$C(CH$_3$)$_2$NHCH$_2$CH(OH)CH$_3$ |

TABLE 1-continued

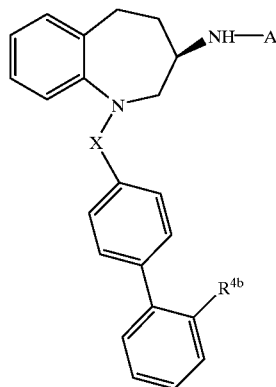

| $R^{4b}$ | X | A |
|---|---|---|
| CN | $CH_2$ | $COCH_2C(CH_3)_2NHCH_2CH(OH)CH_2OH$ |
| $CONH_2$ | $CH_2$ | $COCH_2C(CH_3)_2NHCH_2CH(OH)CH_2OH$ |
| $CH_2CONH_2$ | $CH_2$ | $COCH_2C(CH_3)_2NHCH_2CH(OH)CH_2OH$ |
| $(CH_2)_2CONH_2$ | $CH_2$ | $COCH_2C(CH_3)_2NHCH_2CH(OH)CH_2OH$ |
| $(CH_2)_3CONH_2$ | $CH_2$ | $COCH_2C(CH_3)_2NHCH_2CH(OH)CH_2OH$ |
| $(CH_2)_4CONH_2$ | $CH_2$ | $COCH_2C(CH_3)_2NHCH_2CH(OH)CH_2OH$ |
| $CONHC_2H_5$ | $CH_2$ | $COCH_2C(CH_3)_2NHCH_2CH(OH)CH_2OH$ |
| $CONH(CH_2)_3OH$ | $CH_2$ | $COCH_2C(CH_3)_2NHCH_2CH(OH)CH_2OH$ |
| $CONH(CH_2)_4OH$ | $CH_2$ | $COCH_2C(CH_3)_2NHCH_2CH(OH)CH_2OH$ |
| $CN_4H$ | $CH_2$ | $COCH_2C(CH_3)_2NHCH_2CH(OH)CH_2OH$ |
| $CH_2CN_4H$ | $CH_2$ | $COCH_2C(CH_3)_2NHCH_2CH(OH)CH_2OH$ |
| $(CH_2)_2CN_4H$ | $CH_2$ | $COCH_2C(CH_3)_2NHCH_2CH(OH)CH_2OH$ |
| $(CH_2)_3CN_4H$ | $CH_2$ | $COCH_2C(CH_3)_2NHCH_2CH(OH)CH_2OH$ |
| $(CH_2)_4CN_4H$ | $CH_2$ | $COCH_2C(CH_3)_2NHCH_2CH(OH)CH_2OH$ |
| $CH_2NHCOCH_3$ | $CH_2$ | $COCH_2C(CH_3)_2NHCH_2CH(OH)CH_2OH$ |
| $CH_2NHCONH_2$ | $CH_2$ | $COCH_2C(CH_3)_2NHCH_2CH(OH)CH_2OH$ |
| $CH_2NHCONHCH_3$ | $CH_2$ | $COCH_2C(CH_3)_2NHCH_2CH(OH)CH_2OH$ |
| $CH_2NHCON(CH_3)_2$ | $CH_2$ | $COCH_2C(CH_3)_2NHCH_2CH(OH)CH_2OH$ |
| $CH_2NHCONHC_2H_5$ | $CH_2$ | $COCH_2C(CH_3)_2NHCH_2CH(OH)CH_2OH$ |
| $CH_2NHCONH(CH_2)_2CH_3$ | $CH_2$ | $COCH_2C(CH_3)_2NHCH_2CH(OH)CH_2OH$ |
| $CH_2NHCONH(CH_2)_2OH$ | $CH_2$ | $COCH_2C(CH_3)_2NHCH_2CH(OH)CH_2OH$ |
| $NHCONH_2$ | $CH_2$ | $COCH_2C(CH_3)_2NHCH_2CH(OH)CH_2OH$ |
| $NHCONHCH_3$ | $CH_2$ | $COCH_2C(CH_3)_2NHCH_2CH(OH)CH_2OH$ |
| $NHCONH(CH_2)_2OH$ | $CH_2$ | $COCH_2C(CH_3)_2NHCH_2CH(OH)CH_2OH$ |
| $NHSO_2NH_2$ | $CH_2$ | $COCH_2C(CH_3)_2NHCH_2CH(OH)CH_2OH$ |
| $NHSO_2NHCH_3$ | $CH_2$ | $COCH_2C(CH_3)_2NHCH_2CH(OH)CH_2OH$ |
| $NHSO_2N(CH_3)_2$ | $CH_2$ | $COCH_2C(CH_3)_2NHCH_2CH(OH)CH_2OH$ |
| $NHSO_2N(C_2H_5)_2$ | $CH_2$ | $COCH_2C(CH_3)_2NHCH_2CH(OH)CH_2OH$ |
| CN | CO | $COCH_2C(CH_3)_2NHCH_2CH(OH)CH_2OH$ |
| $CONH_2$ | CO | $COCH_2C(CH_3)_2NHCH_2CH(OH)CH_2OH$ |
| $CH_2CONH_2$ | CO | $COCH_2C(CH_3)_2NHCH_2CH(OH)CH_2OH$ |
| $(CH_2)_2CONH_2$ | CO | $COCH_2C(CH_3)_2NHCH_2CH(OH)CH_2OH$ |
| $(CH_2)_3CONH_2$ | CO | $COCH_2C(CH_3)_2NHCH_2CH(OH)CH_2OH$ |
| $(CH_2)_4CONH_2$ | CO | $COCH_2C(CH_3)_2NHCH_2CH(OH)CH_2OH$ |
| $CONHC_2H_5$ | CO | $COCH_2C(CH_3)_2NHCH_2CH(OH)CH_2OH$ |
| $CONH(CH_2)_3OH$ | CO | $COCH_2C(CH_3)_2NHCH_2CH(OH)CH_2OH$ |
| $CONH(CH_2)_4OH$ | CO | $COCH_2C(CH_3)_2NHCH_2CH(OH)CH_2OH$ |
| $CN_4H$ | CO | $COCH_2C(CH_3)_2NHCH_2CH(OH)CH_2OH$ |
| $CH_2CN_4H$ | CO | $COCH_2C(CH_3)_2NHCH_2CH(OH)CH_2OH$ |
| $(CH_2)_2CN_4H$ | CO | $COCH_2C(CH_3)_2NHCH_2CH(OH)CH_2OH$ |
| $(CH_2)_3CN_4H$ | CO | $COCH_2C(CH_3)_2NHCH_2CH(OH)CH_2OH$ |
| $(CH_2)_4CN_4H$ | CO | $COCH_2C(CH_3)_2NHCH_2CH(OH)CH_2OH$ |
| $CH_2NHCOCH_3$ | CO | $COCH_2C(CH_3)_2NHCH_2CH(OH)CH_2OH$ |
| $CH_2NHCONH_2$ | CO | $COCH_2C(CH_3)_2NHCH_2CH(OH)CH_2OH$ |
| $CH_2NHCONHCH_3$ | CO | $COCH_2C(CH_3)_2NHCH_2CH(OH)CH_2OH$ |
| $CH_2NHCON(CH_3)_2$ | CO | $COCH_2C(CH_3)_2NHCH_2CH(OH)CH_2OH$ |
| $CH_2NHCONHC_2H_5$ | CO | $COCH_2C(CH_3)_2NHCH_2CH(OH)CH_2OH$ |
| $CH_2NHCONH(CH_2)_2CH_3$ | CO | $COCH_2C(CH_3)_2NHCH_2CH(OH)CH_2OH$ |
| $CH_2NHCONH(CH_2)_2OH$ | CO | $COCH_2C(CH_3)_2NHCH_2CH(OH)CH_2OH$ |
| $NHCONH_2$ | CO | $COCH_2C(CH_3)_2NHCH_2CH(OH)CH_2OH$ |
| $NHCONHCH_3$ | CO | $COCH_2C(CH_3)_2NHCH_2CH(OH)CH_2OH$ |
| $NHCONH(CH_2)_2OH$ | CO | $COCH_2C(CH_3)_2NHCH_2CH(OH)CH_2OH$ |
| $NHSO_2NH_2$ | CO | $COCH_2C(CH_3)_2NHCH_2CH(OH)CH_2OH$ |
| $NHSO_2NHCH_3$ | CO | $COCH_2C(CH_3)_2NHCH_2CH(OH)CH_2OH$ |
| $NHSO_2N(CH_3)_2$ | CO | $COCH_2C(CH_3)_2NHCH_2CH(OH)CH_2OH$ |
| $NHSO_2N(C_2H_5)_2$ | CO | $COCH_2C(CH_3)_2NHCH_2CH(OH)CH_2OH$ |

TABLE 2

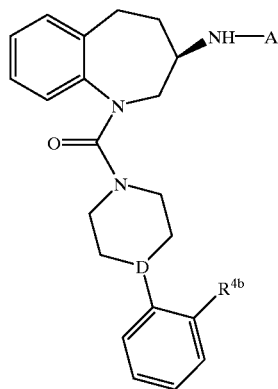

| $R^{4b}$ | D | A |
|---|---|---|
| CN | CH | $COC(CH_3)_2NH_2$ |
| $CONH_2$ | CH | $COC(CH_3)_2NH_2$ |
| $CH_2CONH_2$ | CH | $COC(CH_3)_2NH_2$ |
| $(CH_2)_2CONH_2$ | CH | $COC(CH_3)_2NH_2$ |
| $(CH_2)_3CONH_2$ | CH | $COC(CH_3)_2NH_2$ |
| $(CH_2)_4CONH_2$ | CH | $COC(CH_3)_2NH_2$ |
| $CONHC_2H_5$ | CH | $COC(CH_3)_2NH_2$ |
| $CONH(CH_2)_3OH$ | CH | $COC(CH_3)_2NH_2$ |
| $CONH(CH_2)_4OH$ | CH | $COC(CH_3)_2NH_2$ |
| $CN_4H$ | CH | $COC(CH_3)_2NH_2$ |
| $CH_2CN_4H$ | CH | $COC(CH_3)_2NH_2$ |
| $(CH_2)_2CN_4H$ | CH | $COC(CH_3)_2NH_2$ |
| $(CH_2)_3CN_4H$ | CH | $COC(CH_3)_2NH_2$ |
| $(CH_2)_4CN_4H$ | CH | $COC(CH_3)_2NH_2$ |
| $CH_2NHCOCH_3$ | CH | $COC(CH_3)_2NH_2$ |
| $CH_2NHCONH_2$ | CH | $COC(CH_3)_2NH_2$ |
| $CH_2NHCONHCH_3$ | CH | $COC(CH_3)_2NH_2$ |
| $CH_2NHCON(CH_3)_2$ | CH | $COC(CH_3)_2NH_2$ |
| $CH_2NHCONHC_2H_5$ | CH | $COC(CH_3)_2NH_2$ |
| $CH_2NHCONH(CH_2)_2CH_3$ | CH | $COC(CH_3)_2NH_2$ |
| $CH_2NHCONH(CH_2)_2OH$ | CH | $COC(CH_3)_2NH_2$ |
| $NHCONH_2$ | CH | $COC(CH_3)_2NH_2$ |
| $NHCONHCH_3$ | CH | $COC(CH_3)_2NH_2$ |
| $NHCONH(CH_2)_2OH$ | CH | $COC(CH_3)_2NH_2$ |
| $NHSO_2NH_2$ | CH | $COC(CH_3)_2NH_2$ |
| $NHSO_2NHCH_3$ | CH | $COC(CH_3)_2NH_2$ |
| $NHSO_2N(CH_3)_2$ | CH | $COC(CH_3)_2NH_2$ |
| CN | N | $COC(CH_3)_2NH_2$ |
| $CONH_2$ | N | $COC(CH_3)_2NH_2$ |
| $CH_2CONH_2$ | N | $COC(CH_3)_2NH_2$ |
| $(CH_2)_2CONH_2$ | N | $COC(CH_3)_2NH_2$ |
| $(CH_2)_3CONH_2$ | N | $COC(CH_3)_2NH_2$ |
| $(CH_2)_4CONH_2$ | N | $COC(CH_3)_2NH_2$ |
| $CONHC_2H_5$ | N | $COC(CH_3)_2NH_2$ |
| $CONH(CH_2)_3OH$ | N | $COC(CH_3)_2NH_2$ |
| $CONH(CH_2)_4OH$ | N | $COC(CH_3)_2NH_2$ |
| $CN_4H$ | N | $COC(CH_3)_2NH_2$ |
| $CH_2CN_4H$ | N | $COC(CH_3)_2NH_2$ |
| $(CH_2)_2CN_4H$ | N | $COC(CH_3)_2NH_2$ |
| $(CH_2)_3CN_4H$ | N | $COC(CH_3)_2NH_2$ |
| $(CH_2)_4CN_4H$ | N | $COC(CH_3)_2NH_2$ |
| $CH_2NHCOCH_3$ | N | $COC(CH_3)_2NH_2$ |
| $CH_2NHCONH_2$ | N | $COC(CH_3)_2NH_2$ |
| $CH_2NHCONHCH_3$ | N | $COC(CH_3)_2NH_2$ |
| $CH_2NHCON(CH_3)_2$ | N | $COC(CH_3)_2NH_2$ |
| $CH_2NHCONHC_2H_5$ | N | $COC(CH_3)_2NH_2$ |
| $CH_2NHCONH(CH_2)_2CH_3$ | N | $COC(CH_3)_2NH_2$ |
| $CH_2NHCONH(CH_2)_2OH$ | N | $COC(CH_3)_2NH_2$ |
| $NHCONH_2$ | N | $COC(CH_3)_2NH_2$ |
| $NHCONHCH_3$ | N | $COC(CH_3)_2NH_2$ |
| $NHCONH(CH_2)_2OH$ | N | $COC(CH_3)_2NH_2$ |
| $NHSO_2NH_2$ | N | $COC(CH_3)_2NH_2$ |
| $NHSO_2NHCH_3$ | N | $COC(CH_3)_2NH_2$ |
| $NHSO_2N(CH_3)_2$ | N | $COC(CH_3)_2NH_2$ |
| $NHSO_2N(C_2H_5)_2$ | N | $COC(CH_3)_2NH_2$ |
| CN | CH | $COCH_2C(CH_3)_2NH_2$ |
| $CONH_2$ | CH | $COCH_2C(CH_3)_2NH_2$ |

TABLE 2-continued

| R$^{4b}$ | D | A |
|---|---|---|
| CH$_2$CONH$_2$ | CH | COCH$_2$C(CH$_3$)$_2$NH$_2$ |
| (CH$_2$)$_2$CONH$_2$ | CH | COCH$_2$C(CH$_3$)$_2$NH$_2$ |
| (CH$_2$)$_3$CONH$_2$ | CH | COCH$_2$C(CH$_3$)$_2$NH$_2$ |
| (CH$_2$)$_4$CONH$_2$ | CH | COCH$_2$C(CH$_3$)$_2$NH$_2$ |
| CONHC$_2$H$_5$ | CH | COCH$_2$C(CH$_3$)$_2$NH$_2$ |
| CONH(CH$_2$)$_3$OH | CH | COCH$_2$C(CH$_3$)$_2$NH$_2$ |
| CONH(CH$_2$)$_4$OH | CH | COCH$_2$C(CH$_3$)$_2$NH$_2$ |
| CN$_4$H | CH | COCH$_2$C(CH$_3$)$_2$NH$_2$ |
| CH$_2$CN$_4$H | CH | COCH$_2$C(CH$_3$)$_2$NH$_2$ |
| (CH$_2$)$_2$CN$_4$H | CH | COCH$_2$C(CH$_3$)$_2$NH$_2$ |
| (CH$_2$)$_3$CN$_4$H | CH | COCH$_2$C(CH$_3$)$_2$NH$_2$ |
| (CH$_2$)$_4$CN$_4$H | CH | COCH$_2$C(CH$_3$)$_2$NH$_2$ |
| CH$_2$NHCOCH$_3$ | CH | COCH$_2$C(CH$_3$)$_2$NH$_2$ |
| CH$_2$NHCONH$_2$ | CH | COCH$_2$C(CH$_3$)$_2$NH$_2$ |
| CH$_2$NHCONHCH$_3$ | CH | COCH$_2$C(CH$_3$)$_2$NH$_2$ |
| CH$_2$NHCON(CH$_3$)$_2$ | CH | COCH$_2$C(CH$_3$)$_2$NH$_2$ |
| CH$_2$NHCONHC$_2$H$_5$ | CH | COCH$_2$C(CH$_3$)$_2$NH$_2$ |
| CH$_2$NHCONH(CH$_2$)$_2$CH$_3$ | CH | COCH$_2$C(CH$_3$)$_2$NH$_2$ |
| CH$_2$NHCONH(CH$_2$)$_2$OH | CH | COCH$_2$C(CH$_3$)$_2$NH$_2$ |
| NHCONH$_2$ | CH | COCH$_2$C(CH$_3$)$_2$NH$_2$ |
| NHCONHCH$_3$ | CH | COCH$_2$C(CH$_3$)$_2$NH$_2$ |
| NHCONH(CH$_2$)$_2$OH | CH | COCH$_2$C(CH$_3$)$_2$NH$_2$ |
| NHSO$_2$NH$_2$ | CH | COCH$_2$C(CH$_3$)$_2$NH$_2$ |
| NHSO$_2$NHCH$_3$ | CH | COCH$_2$C(CH$_3$)$_2$NH$_2$ |
| NHSO$_2$N(CH$_3$)$_2$ | CH | COCH$_2$C(CH$_3$)$_2$NH$_2$ |
| CN | N | COCH$_2$C(CH$_3$)$_2$NH$_2$ |
| CONH$_2$ | N | COCH$_2$C(CH$_3$)$_2$NH$_2$ |
| CH$_2$CONH$_2$ | N | COCH$_2$C(CH$_3$)$_2$NH$_2$ |
| (CH$_2$)$_2$CONH$_2$ | N | COCH$_2$C(CH$_3$)$_2$NH$_2$ |
| (CH$_2$)$_3$CONH$_2$ | N | COCH$_2$C(CH$_3$)$_2$NH$_2$ |
| (CH$_2$)$_4$CONH$_2$ | N | COCH$_2$C(CH$_3$)$_2$NH$_2$ |
| CONHC$_2$H$_5$ | N | COCH$_2$C(CH$_3$)$_2$NH$_2$ |
| CONH(CH$_2$)$_3$OH | N | COCH$_2$C(CH$_3$)$_2$NH$_2$ |
| CONH(CH$_2$)$_4$OH | N | COCH$_2$C(CH$_3$)$_2$NH$_2$ |
| CN$_4$H | N | COCH$_2$C(CH$_3$)$_2$NH$_2$ |
| CH$_2$CN$_4$H | N | COCH$_2$C(CH$_3$)$_2$NH$_2$ |
| (CH$_2$)$_2$CN$_4$H | N | COCH$_2$C(CH$_3$)$_2$NH$_2$ |
| (CH$_2$)$_3$CN$_4$H | N | COCH$_2$C(CH$_3$)$_2$NH$_2$ |
| (CH$_2$)$_4$CN$_4$H | N | COCH$_2$C(CH$_3$)$_2$NH$_2$ |
| CH$_2$NHCOCH$_3$ | N | COCH$_2$C(CH$_3$)$_2$NH$_2$ |
| CH$_2$NHCONH$_2$ | N | COCH$_2$C(CH$_3$)$_2$NH$_2$ |
| CH$_2$NHCONHCH$_3$ | N | COCH$_2$C(CH$_3$)$_2$NH$_2$ |
| CH$_2$NHCON(CH$_3$)$_2$ | N | COCH$_2$C(CH$_3$)$_2$NH$_2$ |
| CH$_2$NHCONHC$_2$H$_5$ | N | COCH$_2$C(CH$_3$)$_2$NH$_2$ |
| CH$_2$NHCONH(CH$_2$)$_2$CH$_3$ | N | COCH$_2$C(CH$_3$)$_2$NH$_2$ |
| CH$_2$NHCONH(CH$_2$)$_2$OH | N | COCH$_2$C(CH$_3$)$_2$NH$_2$ |
| NHCONH$_2$ | N | COCH$_2$C(CH$_3$)$_2$NH$_2$ |
| NHCONHCH$_3$ | N | COCH$_2$C(CH$_3$)$_2$NH$_2$ |
| NHCONH(CH$_2$)$_2$OH | N | COCH$_2$C(CH$_3$)$_2$NH$_2$ |
| NHSO$_2$NH$_2$ | N | COCH$_2$C(CH$_3$)$_2$NH$_2$ |
| NHSO$_2$NHCH$_3$ | N | COCH$_2$C(CH$_3$)$_2$NH$_2$ |
| NHSO$_2$N(CH$_3$)$_2$ | N | COCH$_2$C(CH$_3$)$_2$NH$_2$ |
| NHSO$_2$N(C$_2$H$_5$)$_2$ | N | COCH$_2$C(CH$_3$)$_2$NH$_2$ |
| CN | CH | COCH$_2$C(CH$_3$)$_2$NHCH$_2$CH(OH)CH$_3$ |
| CONH$_2$ | CH | COCH$_2$C(CH$_3$)$_2$NHCH$_2$CH(OH)CH$_3$ |
| CH$_2$CONH$_2$ | CH | COCH$_2$C(CH$_3$)$_2$NHCH$_2$CH(OH)CH$_3$ |
| (CH$_2$)$_2$CONH$_2$ | CH | COCH$_2$C(CH$_3$)$_2$NHCH$_2$CH(OH)CH$_3$ |

TABLE 2-continued

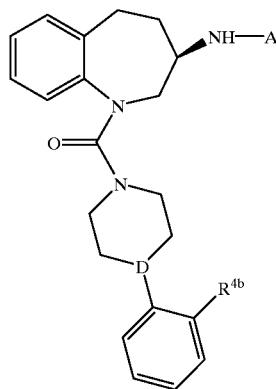

| R[4b] | D | A |
|---|---|---|
| (CH$_2$)$_3$CONH$_2$ | CH | COCH$_2$C(CH$_3$)$_2$NHCH$_2$CH(OH)CH$_3$ |
| (CH$_2$)$_4$CONH$_2$ | CH | COCH$_2$C(CH$_3$)$_2$NHCH$_2$CH(OH)CH$_3$ |
| CONHC$_2$H$_5$ | CH | COCH$_2$C(CH$_3$)$_2$NHCH$_2$CH(OH)CH$_3$ |
| CONH(CH$_2$)$_3$OH | CH | COCH$_2$C(CH$_3$)$_2$NHCH$_2$CH(OH)CH$_3$ |
| CONH(CH$_2$)$_4$OH | CH | COCH$_2$C(CH$_3$)$_2$NHCH$_2$CH(OH)CH$_3$ |
| CN$_4$H | CH | COCH$_2$C(CH$_3$)$_2$NHCH$_2$CH(OH)CH$_3$ |
| CH$_2$CN$_4$H | CH | COCH$_2$C(CH$_3$)$_2$NHCH$_2$CH(OH)CH$_3$ |
| (CH$_2$)$_2$CN$_4$H | CH | COCH$_2$C(CH$_3$)$_2$NHCH$_2$CH(OH)CH$_3$ |
| (CH$_2$)$_3$CN$_4$H | CH | COCH$_2$C(CH$_3$)$_2$NHCH$_2$CH(OH)CH$_3$ |
| (CH$_2$)$_4$CN$_4$H | CH | COCH$_2$C(CH$_3$)$_2$NHCH$_2$CH(OH)CH$_3$ |
| CH$_2$NHCOCH$_3$ | CH | COCH$_2$C(CH$_3$)$_2$NHCH$_2$CH(OH)CH$_3$ |
| CH$_2$NHCONH$_2$ | CH | COCH$_2$C(CH$_3$)$_2$NHCH$_2$CH(OH)CH$_3$ |
| CH$_2$NHCONHCH$_3$ | CH | COCH$_2$C(CH$_3$)$_2$NHCH$_2$CH(OH)CH$_3$ |
| CH$_2$NHCON(CH$_3$)$_2$ | CH | COCH$_2$C(CH$_3$)$_2$NHCH$_2$CH(OH)CH$_3$ |
| CH$_2$NHCONHC$_2$H$_5$ | CH | COCH$_2$C(CH$_3$)$_2$NHCH$_2$CH(OH)CH$_3$ |
| CH$_2$NHCONH(CH$_2$)$_2$CH$_3$ | CH | COCH$_2$C(CH$_3$)$_2$NHCH$_2$CH(OH)CH$_3$ |
| CH$_2$NHCONH(CH$_2$)$_2$OH | CH | COCH$_2$C(CH$_3$)$_2$NHCH$_2$CH(OH)CH$_3$ |
| NHCONH$_2$ | CH | COCH$_2$C(CH$_3$)$_2$NHCH$_2$CH(OH)CH$_3$ |
| NHCONHCH$_3$ | CH | COCH$_2$C(CH$_3$)$_2$NHCH$_2$CH(OH)CH$_3$ |
| NHCONH(CH$_2$)$_2$OH | CH | COCH$_2$C(CH$_3$)$_2$NHCH$_2$CH(OH)CH$_3$ |
| NHSO$_2$NH$_2$ | CH | COCH$_2$C(CH$_3$)$_2$NHCH$_2$CH(OH)CH$_3$ |
| NHSO$_2$NHCH$_3$ | CH | COCH$_2$C(CH$_3$)$_2$NHCH$_2$CH(OH)CH$_3$ |
| NHSO$_2$N(CH$_3$)$_2$ | CH | COCH$_2$C(CH$_3$)$_2$NHCH$_2$CH(OH)CH$_3$ |
| CN | N | COCH$_2$C(CH$_3$)$_2$NHCH$_2$CH(OH)CH$_3$ |
| CONH$_2$ | N | COCH$_2$C(CH$_3$)$_2$NHCH$_2$CH(OH)CH$_3$ |
| CH$_2$CONH$_2$ | N | COCH$_2$C(CH$_3$)$_2$NHCH$_2$CH(OH)CH$_3$ |
| (CH$_2$)$_2$CONH$_2$ | N | COCH$_2$C(CH$_3$)$_2$NHCH$_2$CH(OH)CH$_3$ |
| (CH$_2$)$_3$CONH$_2$ | N | COCH$_2$C(CH$_3$)$_2$NHCH$_2$CH(OH)CH$_3$ |
| (CH$_2$)$_4$CONH$_2$ | N | COCH$_2$C(CH$_3$)$_2$NHCH$_2$CH(OH)CH$_3$ |
| CONHC$_2$H$_5$ | N | COCH$_2$C(CH$_3$)$_2$NHCH$_2$CH(OH)CH$_3$ |
| CONH(CH$_2$)$_3$OH | N | COCH$_2$C(CH$_3$)$_2$NHCH$_2$CH(OH)CH$_3$ |
| CONH(CH$_2$)$_4$OH | N | COCH$_2$C(CH$_3$)$_2$NHCH$_2$CH(OH)CH$_3$ |
| CN$_4$H | N | COCH$_2$C(CH$_3$)$_2$NHCH$_2$CH(OH)CH$_3$ |
| CH$_2$CN$_4$H | N | COCH$_2$C(CH$_3$)$_2$NHCH$_2$CH(OH)CH$_3$ |
| (CH$_2$)$_2$CN$_4$H | N | COCH$_2$C(CH$_3$)$_2$NHCH$_2$CH(OH)CH$_3$ |
| (CH$_2$)$_3$CN$_4$H | N | COCH$_2$C(CH$_3$)$_2$NHCH$_2$CH(OH)CH$_3$ |
| (CH$_2$)$_4$CN$_4$H | N | COCH$_2$C(CH$_3$)$_2$NHCH$_2$CH(OH)CH$_3$ |
| CH$_2$NHCOCH$_3$ | N | COCH$_2$C(CH$_3$)$_2$NHCH$_2$CH(OH)CH$_3$ |
| CH$_2$NHCONH$_2$ | N | COCH$_2$C(CH$_3$)$_2$NHCH$_2$CH(OH)CH$_3$ |
| CH$_2$NHCONHCH$_3$ | N | COCH$_2$C(CH$_3$)$_2$NHCH$_2$CH(OH)CH$_3$ |
| CH$_2$NHCON(CH$_3$)$_2$ | N | COCH$_2$C(CH$_3$)$_2$NHCH$_2$CH(OH)CH$_3$ |
| CH$_2$NHCONHC$_2$H$_5$ | N | COCH$_2$C(CH$_3$)$_2$NHCH$_2$CH(OH)CH$_3$ |
| CH$_2$NHCONH(CH$_2$)$_2$CH$_3$ | N | COCH$_2$C(CH$_3$)$_2$NHCH$_2$CH(OH)CH$_3$ |
| CH$_2$NHCONH(CH$_2$)$_2$OH | N | COCH$_2$C(CH$_3$)$_2$NHCH$_2$CH(OH)CH$_3$ |
| NHCONH$_2$ | N | COCH$_2$C(CH$_3$)$_2$NHCH$_2$CH(OH)CH$_3$ |
| NHCONHCH$_3$ | N | COCH$_2$C(CH$_3$)$_2$NHCH$_2$CH(OH)CH$_3$ |
| NHCONH(CH$_2$)$_2$OH | N | COCH$_2$C(CH$_3$)$_2$NHCH$_2$CH(OH)CH$_3$ |
| NHSO$_2$NH$_2$ | N | COCH$_2$C(CH$_3$)$_2$NHCH$_2$CH(OH)CH$_3$ |
| NHSO$_2$NHCH$_3$ | N | COCH$_2$C(CH$_3$)$_2$NHCH$_2$CH(OH)CH$_3$ |
| NHSO$_2$N(CH$_3$)$_2$ | N | COCH$_2$C(CH$_3$)$_2$NHCH$_2$CH(OH)CH$_3$ |
| NHSO$_2$N(C$_2$H$_5$)$_2$ | N | COCH$_2$C(CH$_3$)$_2$NHCH$_2$CH(OH)CH$_3$ |
| CN | CH | COCH$_2$C(CH$_3$)$_2$NHCH$_2$CH(OH)CH$_2$OH |
| CONH$_2$ | CH | COCH$_2$C(CH$_3$)$_2$NHCH$_2$CH(OH)CH$_2$OH |
| CH$_2$CONH$_2$ | CH | COCH$_2$C(CH$_3$)$_2$NHCH$_2$CH(OH)CH$_2$OH |
| (CH$_2$)$_2$CONH$_2$ | CH | COCH$_2$C(CH$_3$)$_2$NHCH$_2$CH(OH)CH$_2$OH |
| (CH$_2$)$_3$CONH$_2$ | CH | COCH$_2$C(CH$_3$)$_2$NHCH$_2$CH(OH)CH$_2$OH |
| (CH$_2$)$_4$CONH$_2$ | CH | COCH$_2$C(CH$_3$)$_2$NHCH$_2$CH(OH)CH$_2$OH |

TABLE 2-continued

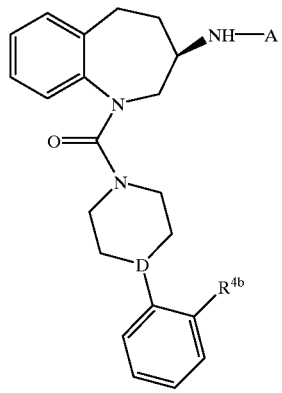

| $R^{4b}$ | D | A |
| --- | --- | --- |
| CONHC$_2$H$_5$ | CH | COCH$_2$C(CH$_3$)$_2$NHCH$_2$CH(OH)CH$_2$OH |
| CONH(CH$_2$)$_3$OH | CH | COCH$_2$C(CH$_3$)$_2$NHCH$_2$CH(OH)CH$_2$OH |
| CONH(CH$_2$)$_4$OH | CH | COCH$_2$C(CH$_3$)$_2$NHCH$_2$CH(OH)CH$_2$OH |
| CN$_4$H | CH | COCH$_2$C(CH$_3$)$_2$NHCH$_2$CH(OH)CH$_2$OH |
| CH$_2$CN$_4$H | CH | COCH$_2$C(CH$_3$)$_2$NHCH$_2$CH(OH)CH$_2$OH |
| (CH$_2$)$_2$CN$_4$H | CH | COCH$_2$C(CH$_3$)$_2$NHCH$_2$CH(OH)CH$_2$OH |
| (CH$_2$)$_3$CN$_4$H | CH | COCH$_2$C(CH$_3$)$_2$NHCH$_2$CH(OH)CH$_2$OH |
| (CH$_2$)$_4$CN$_4$H | CH | COCH$_2$C(CH$_3$)$_2$NHCH$_2$CH(OH)CH$_2$OH |
| CH$_2$NHCOCH$_3$ | CH | COCH$_2$C(CH$_3$)$_2$NHCH$_2$CH(OH)CH$_2$OH |
| CH$_2$NHCONH$_2$ | CH | COCH$_2$C(CH$_3$)$_2$NHCH$_2$CH(OH)CH$_2$OH |
| CH$_2$NHCONHCH$_3$ | CH | COCH$_2$C(CH$_3$)$_2$NHCH$_2$CH(OH)CH$_2$OH |
| CH$_2$NHCON(CH$_3$)$_2$ | CH | COCH$_2$C(CH$_3$)$_2$NHCH$_2$CH(OH)CH$_2$OH |
| CH$_2$NHCONHC$_2$H$_5$ | CH | COCH$_2$C(CH$_3$)$_2$NHCH$_2$CH(OH)CH$_2$OH |
| CH$_2$NHCONH(CH$_2$)$_2$CH$_3$ | CH | COCH$_2$C(CH$_3$)$_2$NHCH$_2$CH(OH)CH$_2$OH |
| CH$_2$NHCONH(CH$_2$)$_2$OH | CH | COCH$_2$C(CH$_3$)$_2$NHCH$_2$CH(OH)CH$_2$OH |
| NHCONH$_2$ | CH | COCH$_2$C(CH$_3$)$_2$NHCH$_2$CH(OH)CH$_2$OH |
| NHCONHCH$_3$ | CH | COCH$_2$C(CH$_3$)$_2$NHCH$_2$CH(OH)CH$_2$OH |
| NHCONH(CH$_2$)$_2$OH | CH | COCH$_2$C(CH$_3$)$_2$NHCH$_2$CH(OH)CH$_2$OH |
| NHSO$_2$NH$_2$ | CH | COCH$_2$C(CH$_3$)$_2$NHCH$_2$CH(OH)CH$_2$OH |
| NHSO$_2$NHCH$_3$ | CH | COCH$_2$C(CH$_3$)$_2$NHCH$_2$CH(OH)CH$_2$OH |
| NHSO$_2$N(CH$_3$)$_2$ | CH | COCH$_2$C(CH$_3$)$_2$NHCH$_2$CH(OH)CH$_2$OH |
| CN | N | COCH$_2$C(CH$_3$)$_2$NHCH$_2$CH(OH)CH$_2$OH |
| CONH$_2$ | N | COCH$_2$C(CH$_3$)$_2$NHCH$_2$CH(OH)CH$_2$OH |
| CH$_2$CONH$_2$ | N | COCH$_2$C(CH$_3$)$_2$NHCH$_2$CH(OH)CH$_2$OH |
| (CH$_2$)$_2$CONH$_2$ | N | COCH$_2$C(CH$_3$)$_2$NHCH$_2$CH(OH)CH$_2$OH |
| (CH$_2$)$_3$CONH$_2$ | N | COCH$_2$C(CH$_3$)$_2$NHCH$_2$CH(OH)CH$_2$OH |
| (CH$_2$)$_4$CONH$_2$ | N | COCH$_2$C(CH$_3$)$_2$NHCH$_2$CH(OH)CH$_2$OH |
| CONHC$_2$H$_5$ | N | COCH$_2$C(CH$_3$)$_2$NHCH$_2$CH(OH)CH$_2$OH |
| CONH(CH$_2$)$_3$OH | N | COCH$_2$C(CH$_3$)$_2$NHCH$_2$CH(OH)CH$_2$OH |
| CONH(CH$_2$)$_4$OH | N | COCH$_2$C(CH$_3$)$_2$NHCH$_2$CH(OH)CH$_2$OH |
| CN$_4$H | N | COCH$_2$C(CH$_3$)$_2$NHCH$_2$CH(OH)CH$_2$OH |
| CH$_2$CN$_4$H | N | COCH$_2$C(CH$_3$)$_2$NHCH$_2$CH(OH)CH$_2$OH |
| (CH$_2$)$_2$CN$_4$H | N | COCH$_2$C(CH$_3$)$_2$NHCH$_2$CH(OH)CH$_2$OH |
| (CH$_2$)$_3$CN$_4$H | N | COCH$_2$C(CH$_3$)$_2$NHCH$_2$CH(OH)CH$_2$OH |
| (CH$_2$)$_4$CN$_4$H | N | COCH$_2$C(CH$_3$)$_2$NHCH$_2$CH(OH)CH$_2$OH |
| CH$_2$NHCOCH$_3$ | N | COCH$_2$C(CH$_3$)$_2$NHCH$_2$CH(OH)CH$_2$OH |
| CH$_2$NHCONH$_2$ | N | COCH$_2$C(CH$_3$)$_2$NHCH$_2$CH(OH)CH$_2$OH |
| CH$_2$NHCONHCH$_3$ | N | COCH$_2$C(CH$_3$)$_2$NHCH$_2$CH(OH)CH$_2$OH |
| CH$_2$NHCON(CH$_3$)$_2$ | N | COCH$_2$C(CH$_3$)$_2$NHCH$_2$CH(OH)CH$_2$OH |
| CH$_2$NHCONHC$_2$H$_5$ | N | COCH$_2$C(CH$_3$)$_2$NHCH$_2$CH(OH)CH$_2$OH |
| CH$_2$NHCONH(CH$_2$)$_2$CH$_3$ | N | COCH$_2$C(CH$_3$)$_2$NHCH$_2$CH(OH)CH$_2$OH |
| CH$_2$NHCONH(CH$_2$)$_2$OH | N | COCH$_2$C(CH$_3$)$_2$NHCH$_2$CH(OH)CH$_2$OH |
| NHCONH$_2$ | N | COCH$_2$C(CH$_3$)$_2$NHCH$_2$CH(OH)CH$_2$OH |
| NHCONHCH$_3$ | N | COCH$_2$C(CH$_3$)$_2$NHCH$_2$CH(OH)CH$_2$OH |
| NHCONH(CH$_2$)$_2$OH | N | COCH$_2$C(CH$_3$)$_2$NHCH$_2$CH(OH)CH$_2$OH |
| NHSO$_2$NH$_2$ | N | COCH$_2$C(CH$_3$)$_2$NHCH$_2$CH(OH)CH$_2$OH |
| NHSO$_2$NHCH$_3$ | N | COCH$_2$C(CH$_3$)$_2$NHCH$_2$CH(OH)CH$_2$OH |
| NHSO$_2$N(CH$_3$)$_2$ | N | COCH$_2$C(CH$_3$)$_2$NHCH$_2$CH(OH)CH$_2$OH |
| NHSO$_2$N(C$_2$H$_5$)$_2$ | N | COCH$_2$C(CH$_3$)$_2$NHCH$_2$CH(OH)CH$_2$OH |

TABLE 3

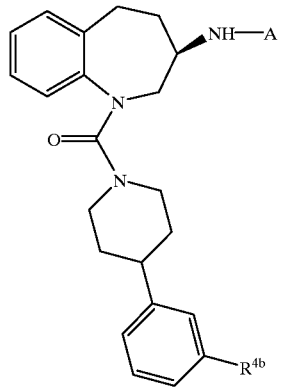

| R4b | A |
|---|---|
| CN | COC(CH3)2NH2 |
| CONH2 | COC(CH3)2NH2 |
| CH2CONH2 | COC(CH3)2NH2 |
| (CH2)2CONH2 | COC(CH3)2NH2 |
| (CH2)3CONH2 | COC(CH3)2NH2 |
| (CH2)4CONH2 | COC(CH3)2NH2 |
| CONHC2H5 | COC(CH3)2NH2 |
| CONH(CH2)3OH | COC(CH3)2NH2 |
| CONH(CH2)4OH | COC(CH3)2NH2 |
| CN4H | COC(CH3)2NH2 |
| CH2CN4H | COC(CH3)2NH2 |
| (CH2)2CN4H | COC(CH3)2NH2 |
| (CH2)3CN4H | COC(CH3)2NH2 |
| (CH2)4CN4H | COC(CH3)2NH2 |
| CH2NHCOCH3 | COC(CH3)2NH2 |
| CH2NHCONH2 | COC(CH3)2NH2 |
| CH2NHCONHCH3 | COC(CH3)2NH2 |
| CH2NHCON(CH3)2 | COC(CH3)2NH2 |
| CH2NHCONHC2H5 | COC(CH3)2NH2 |
| CH2NHCONH(CH2)2CH3 | COC(CH3)2NH2 |
| CH2NHCONH(CH2)2OH | COC(CH3)2NH2 |
| NHCONH2 | COC(CH3)2NH2 |
| NHCONHCH3 | COC(CH3)2NH2 |
| NHCONH(CH2)2OH | COC(CH3)2NH2 |
| NHSO2NH2 | COC(CH3)2NH2 |
| NHSO2NHCH3 | COC(CH3)2NH2 |
| NHSO2N(CH3)2 | COC(CH3)2NH2 |
| CN | COCH2C(CH3)2NH2 |
| CONH2 | COCH2C(CH3)2NH2 |
| CH2CONH2 | COCH2C(CH3)2NH2 |
| (CH2)2CONH2 | COCH2C(CH3)2NH2 |
| (CH2)3CONH2 | COCH2C(CH3)2NH2 |
| (CH2)4CONH2 | COCH2C(CH3)2NH2 |
| CONHC2H5 | COCH2C(CH3)2NH2 |
| CONH(CH2)3OH | COCH2C(CH3)2NH2 |
| CONH(CH2)4OH | COCH2C(CH3)2NH2 |
| CN4H | COCH2C(CH3)2NH2 |
| CH2CN4H | COCH2C(CH3)2NH2 |
| (CH2)2CN4H | COCH2C(CH3)2NH2 |
| (CH2)3CN4H | COCH2C(CH3)2NH2 |
| (CH2)4CN4H | COCH2C(CH3)2NH2 |
| CH2NHCOCH3 | COCH2C(CH3)2NH2 |
| CH2NHCONH2 | COCH2C(CH3)2NH2 |
| CH2NHCONHCH3 | COCH2C(CH3)2NH2 |
| CH2NHCON(CH3)2 | COCH2C(CH3)2NH2 |
| CH2NHCONHC2H5 | COCH2C(CH3)2NH2 |
| CH2NHCONH(CH2)2CH3 | COCH2C(CH3)2NH2 |
| CH2NHCONH(CH2)2OH | COCH2C(CH3)2NH2 |
| NHCONH2 | COCH2C(CH3)2NH2 |
| NHCONHCH3 | COCH2C(CH3)2NH2 |
| NHCONH(CH2)2OH | COCH2C(CH3)2NH2 |
| NHSO2NH2 | COCH2C(CH3)2NH2 |
| NHSO2NHCH3 | COCH2C(CH3)2NH2 |
| NHSO2N(CH3)2 | COCH2C(CH3)2NH2 |
| NHSO2N(C2H5)2 | COCH2C(CH3)2NH2 |
| CN | COCH2C(CH3)2NHCH2CH(OH)CH3 |
| CONH2 | COCH2C(CH3)2NHCH2CH(OH)CH3 |

TABLE 3-continued

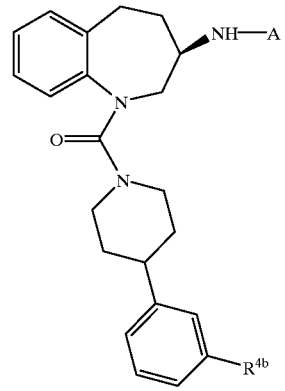

| R4b | A |
|---|---|
| CH2CONH2 | COCH2C(CH3)2NHCH2CH(OH)CH3 |
| (CH2)2CONH2 | COCH2C(CH3)2NHCH2CH(OH)CH3 |
| (CH2)3CONH2 | COCH2C(CH3)2NHCH2CH(OH)CH3 |
| (CH2)4CONH2 | COCH2C(CH3)2NHCH2CH(OH)CH3 |
| CONHC2H5 | COCH2C(CH3)2NHCH2CH(OH)CH3 |
| CONH(CH2)3OH | COCH2C(CH3)2NHCH2CH(OH)CH3 |
| CONH(CH2)4OH | COCH2C(CH3)2NHCH2CH(OH)CH3 |
| CN4H | COCH2C(CH3)2NHCH2CH(OH)CH3 |
| CH2CN4H | COCH2C(CH3)2NHCH2CH(OH)CH3 |
| (CH2)2CN4H | COCH2C(CH3)2NHCH2CH(OH)CH3 |
| (CH2)3CN4H | COCH2C(CH3)2NHCH2CH(OH)CH3 |
| (CH2)4CN4H | COCH2C(CH3)2NHCH2CH(OH)CH3 |
| CH2NHCOCH3 | COCH2C(CH3)2NHCH2CH(OH)CH3 |
| CH2NHCONH2 | COCH2C(CH3)2NHCH2CH(OH)CH3 |
| CH2NHCONHCH3 | COCH2C(CH3)2NHCH2CH(OH)CH3 |
| CH2NHCON(CH3)2 | COCH2C(CH3)2NHCH2CH(OH)CH3 |
| CH2NHCONHC2H5 | COCH2C(CH3)2NHCH2CH(OH)CH3 |
| CH2NHCONH(CH2)2CH3 | COCH2C(CH3)2NHCH2CH(OH)CH3 |
| CH2NHCONH(CH2)2OH | COCH2C(CH3)2NHCH2CH(OH)CH3 |
| NHCONH2 | COCH2C(CH3)2NHCH2CH(OH)CH3 |
| NHCONHCH3 | COCH2C(CH3)2NHCH2CH(OH)CH3 |
| NHCONH(CH2)2OH | COCH2C(CH3)2NHCH2CH(OH)CH3 |
| NHSO2NH2 | COCH2C(CH3)2NHCH2CH(OH)CH3 |
| NHSO2NHCH3 | COCH2C(CH3)2NHCH2CH(OH)CH3 |
| NHSO2N(CH3)2 | COCH2C(CH3)2NHCH2CH(OH)CH3 |
| CN | COCH2C(CH3)2NHCH2CH(OH)CH2OH |
| CONH2 | COCH2C(CH3)2NHCH2CH(OH)CH2OH |
| CH2CONH2 | COCH2C(CH3)2NHCH2CH(OH)CH2OH |
| (CH2)2CONH2 | COCH2C(CH3)2NHCH2CH(OH)CH2OH |
| (CH2)3CONH2 | COCH2C(CH3)2NHCH2CH(OH)CH2OH |
| (CH2)4CONH2 | COCH2C(CH3)2NHCH2CH(OH)CH2OH |
| CONHC2H5 | COCH2C(CH3)2NHCH2CH(OH)CH2OH |
| CONH(CH2)3OH | COCH2C(CH3)2NHCH2CH(OH)CH2OH |
| CONH(CH2)4OH | COCH2C(CH3)2NHCH2CH(OH)CH2OH |
| CN4H | COCH2C(CH3)2NHCH2CH(OH)CH2OH |
| CH2CN4H | COCH2C(CH3)2NHCH2CH(OH)CH2OH |
| (CH2)2CN4H | COCH2C(CH3)2NHCH2CH(OH)CH2OH |
| (CH2)3CN4H | COCH2C(CH3)2NHCH2CH(OH)CH2OH |
| (CH2)4CN4H | COCH2C(CH3)2NHCH2CH(OH)CH2OH |
| CH2NHCOCH3 | COCH2C(CH3)2NHCH2CH(OH)CH2OH |
| CH2NHCONH2 | COCH2C(CH3)2NHCH2CH(OH)CH2OH |
| CH2NHCONHCH3 | COCH2C(CH3)2NHCH2CH(OH)CH2OH |
| CH2NHCON(CH3)2 | COCH2C(CH3)2NHCH2CH(OH)CH2OH |
| CH2NHCONHC2H5 | COCH2C(CH3)2NHCH2CH(OH)CH2OH |
| CH2NHCONH(CH2)2CH3 | COCH2C(CH3)2NHCH2CH(OH)CH2OH |
| CH2NHCONH(CH2)2OH | COCH2C(CH3)2NHCH2CH(OH)CH2OH |
| NHCONH2 | COCH2C(CH3)2NHCH2CH(OH)CH2OH |
| NHCONHCH3 | COCH2C(CH3)2NHCH2CH(OH)CH2OH |
| NHCONH(CH2)2OH | COCH2C(CH3)2NHCH2CH(OH)CH2OH |
| NHSO2NH2 | COCH2C(CH3)2NHCH2CH(OH)CH2OH |
| NHSO2NHCH3 | COCH2C(CH3)2NHCH2CH(OH)CH2OH |
| NHSO2N(CH3)2 | COCH2C(CH3)2NHCH2CH(OH)CH2OH |
| NHSO2N(C2H5)2 | COCH2C(CH3)2NHCH2CH(OH)CH2OH |

TABLE 4

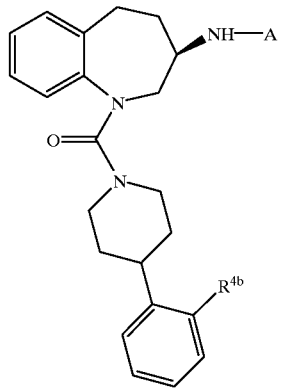

| $R^{4b}$ | A |
|---|---|
| CN | COC(CH$_3$)$_2$NH$_2$ |
| CONH$_2$ | COC(CH$_3$)$_2$NH$_2$ |
| CH$_2$CONH$_2$ | COC(CH$_3$)$_2$NH$_2$ |
| (CH$_2$)$_2$CONH$_2$ | COC(CH$_3$)$_2$NH$_2$ |
| (CH$_2$)$_3$CONH$_2$ | COC(CH$_3$)$_2$NH$_2$ |
| (CH$_2$)$_4$CONH$_2$ | COC(CH$_3$)$_2$NH$_2$ |
| CONHC$_2$H$_5$ | COC(CH$_3$)$_2$NH$_2$ |
| CONH(CH$_2$)$_3$OH | COC(CH$_3$)$_2$NH$_2$ |
| CONH(CH$_2$)$_4$OH | COC(CH$_3$)$_2$NH$_2$ |
| CN$_4$H | COC(CH$_3$)$_2$NH$_2$ |
| CH$_2$CN$_4$H | COC(CH$_3$)$_2$NH$_2$ |
| (CH$_2$)$_2$CN$_4$H | COC(CH$_3$)$_2$NH$_2$ |
| (CH$_2$)$_3$CN$_4$H | COC(CH$_3$)$_2$NH$_2$ |
| (CH$_2$)$_4$CN$_4$H | COC(CH$_3$)$_2$NH$_2$ |
| CH$_2$NHCOCH$_3$ | COC(CH$_3$)$_2$NH$_2$ |
| CH$_2$NHCONH$_2$ | COC(CH$_3$)$_2$NH$_2$ |
| CH$_2$NHCONHCH$_3$ | COC(CH$_3$)$_2$NH$_2$ |
| CH$_2$NHCON(CH$_3$)$_2$ | COC(CH$_3$)$_2$NH$_2$ |
| CH$_2$NHCONHC$_2$H$_5$ | COC(CH$_3$)$_2$NH$_2$ |
| CH$_2$NHCONH(CH$_2$)$_2$CH$_3$ | COC(CH$_3$)$_2$NH$_2$ |
| CH$_2$NHCONH(CH$_2$)$_2$OH | COC(CH$_3$)$_2$NH$_2$ |
| NHCONH$_2$ | COC(CH$_3$)$_2$NH$_2$ |
| NHCONHCH$_3$ | COC(CH$_3$)$_2$NH$_2$ |
| NHCONH(CH$_2$)$_2$OH | COC(CH$_3$)$_2$NH$_2$ |
| NHSO$_2$NH$_2$ | COC(CH$_3$)$_2$NH$_2$ |
| NHSO$_2$NHCH$_3$ | COC(CH$_3$)$_2$NH$_2$ |
| NHSO$_2$N(CH$_3$)$_2$ | COC(CH$_3$)$_2$NH$_2$ |
| CN | COCH$_2$C(CH$_3$)$_2$NH$_2$ |
| CONH$_2$ | COCH$_2$C(CH$_3$)$_2$NH$_2$ |
| CH$_2$CONH$_2$ | COCH$_2$C(CH$_3$)$_2$NH$_2$ |
| (CH$_2$)$_2$CONH$_2$ | COCH$_2$C(CH$_3$)$_2$NH$_2$ |
| (CH$_2$)$_3$CONH$_2$ | COCH$_2$C(CH$_3$)$_2$NH$_2$ |
| (CH$_2$)$_4$CONH$_2$ | COCH$_2$C(CH$_3$)$_2$NH$_2$ |
| CONHC$_2$H$_5$ | COCH$_2$C(CH$_3$)$_2$NH$_2$ |
| CONH(CH$_2$)$_3$OH | COCH$_2$C(CH$_3$)$_2$NH$_2$ |
| CONH(CH$_2$)$_4$OH | COCH$_2$C(CH$_3$)$_2$NH$_2$ |
| CN$_4$H | COCH$_2$C(CH$_3$)$_2$NH$_2$ |
| CH$_2$CN$_4$H | COCH$_2$C(CH$_3$)$_2$NH$_2$ |
| (CH$_2$)$_2$CN$_4$H | COCH$_2$C(CH$_3$)$_2$NH$_2$ |
| (CH$_2$)$_3$CN$_4$H | COCH$_2$C(CH$_3$)$_2$NH$_2$ |
| (CH$_2$)$_4$CN$_4$H | COCH$_2$C(CH$_3$)$_2$NH$_2$ |
| CH$_2$NHCOCH$_3$ | COCH$_2$C(CH$_3$)$_2$NH$_2$ |
| CH$_2$NHCONH$_2$ | COCH$_2$C(CH$_3$)$_2$NH$_2$ |
| CH$_2$NHCONHCH$_3$ | COCH$_2$C(CH$_3$)$_2$NH$_2$ |
| CH$_2$NHCON(CH$_3$)$_2$ | COCH$_2$C(CH$_3$)$_2$NH$_2$ |
| CH$_2$NHCONHC$_2$H$_5$ | COCH$_2$C(CH$_3$)$_2$NH$_2$ |
| CH$_2$NHCONH(CH$_2$)$_2$CH$_3$ | COCH$_2$C(CH$_3$)$_2$NH$_2$ |
| CH$_2$NHCONH(CH$_2$)$_2$OH | COCH$_2$C(CH$_3$)$_2$NH$_2$ |
| NHCONH$_2$ | COCH$_2$C(CH$_3$)$_2$NH$_2$ |
| NHCONHCH$_3$ | COCH$_2$C(CH$_3$)$_2$NH$_2$ |
| NHCONH(CH$_2$)$_2$OH | COCH$_2$C(CH$_3$)$_2$NH$_2$ |
| NHSO$_2$NH$_2$ | COCH$_2$C(CH$_3$)$_2$NH$_2$ |
| NHSO$_2$NHCH$_3$ | COCH$_2$C(CH$_3$)$_2$NH$_2$ |
| NHSO$_2$N(CH$_3$)$_2$ | COCH$_2$C(CH$_3$)$_2$NH$_2$ |
| NHSO$_2$N(C$_2$H$_5$)$_2$ | COCH$_2$C(CH$_3$)$_2$NH$_2$ |
| CN | COCH$_2$C(CH$_3$)$_2$NHCH$_2$CH(OH)CH$_3$ |
| CONH$_2$ | COCH$_2$C(CH$_3$)$_2$NHCH$_2$CH(OH)CH$_3$ |

TABLE 4-continued

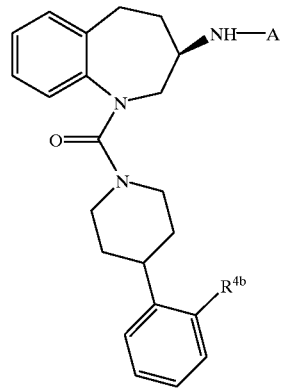

| $R^{4b}$ | A |
|---|---|
| CH$_2$CONH$_2$ | COCH$_2$C(CH$_3$)$_2$NHCH$_2$CH(OH)CH$_3$ |
| (CH$_2$)$_2$CONH$_2$ | COCH$_2$C(CH$_3$)$_2$NHCH$_2$CH(OH)CH$_3$ |
| (CH$_2$)$_3$CONH$_2$ | COCH$_2$C(CH$_3$)$_2$NHCH$_2$CH(OH)CH$_3$ |
| (CH$_2$)$_4$CONH$_2$ | COCH$_2$C(CH$_3$)$_2$NHCH$_2$CH(OH)CH$_3$ |
| CONHC$_2$H$_5$ | COCH$_2$C(CH$_3$)$_2$NHCH$_2$CH(OH)CH$_3$ |
| CONH(CH$_2$)$_3$OH | COCH$_2$C(CH$_3$)$_2$NHCH$_2$CH(OH)CH$_3$ |
| CONH(CH$_2$)$_4$OH | COCH$_2$C(CH$_3$)$_2$NHCH$_2$CH(OH)CH$_3$ |
| CN$_4$H | COCH$_2$C(CH$_3$)$_2$NHCH$_2$CH(OH)CH$_3$ |
| CH$_2$CN$_4$H | COCH$_2$C(CH$_3$)$_2$NHCH$_2$CH(OH)CH$_3$ |
| (CH$_2$)$_2$CN$_4$H | COCH$_2$C(CH$_3$)$_2$NHCH$_2$CH(OH)CH$_3$ |
| (CH$_2$)$_3$CN$_4$H | COCH$_2$C(CH$_3$)$_2$NHCH$_2$CH(OH)CH$_3$ |
| (CH$_2$)$_4$CN$_4$H | COCH$_2$C(CH$_3$)$_2$NHCH$_2$CH(OH)CH$_3$ |
| CH$_2$NHCOCH$_3$ | COCH$_2$C(CH$_3$)$_2$NHCH$_2$CH(OH)CH$_3$ |
| CH$_2$NHCONH$_2$ | COCH$_2$C(CH$_3$)$_2$NHCH$_2$CH(OH)CH$_3$ |
| CH$_2$NHCONHCH$_3$ | COCH$_2$C(CH$_3$)$_2$NHCH$_2$CH(OH)CH$_3$ |
| CH$_2$NHCON(CH$_3$)$_2$ | COCH$_2$C(CH$_3$)$_2$NHCH$_2$CH(OH)CH$_3$ |
| CH$_2$NHCONHC$_2$H$_5$ | COCH$_2$C(CH$_3$)$_2$NHCH$_2$CH(OH)CH$_3$ |
| CH$_2$NHCONH(CH$_2$)$_2$CH$_3$ | COCH$_2$C(CH$_3$)$_2$NHCH$_2$CH(OH)CH$_3$ |
| CH$_2$NHCONH(CH$_2$)$_2$OH | COCH$_2$C(CH$_3$)$_2$NHCH$_2$CH(OH)CH$_3$ |
| NHCONH$_2$ | COCH$_2$C(CH$_3$)$_2$NHCH$_2$CH(OH)CH$_3$ |
| NHCONHCH$_3$ | COCH$_2$C(CH$_3$)$_2$NHCH$_2$CH(OH)CH$_3$ |
| NHCONH(CH$_2$)$_2$OH | COCH$_2$C(CH$_3$)$_2$NHCH$_2$CH(OH)CH$_3$ |
| NHSO$_2$NH$_2$ | COCH$_2$C(CH$_3$)$_2$NHCH$_2$CH(OH)CH$_3$ |
| NHSO$_2$NHCH$_3$ | COCH$_2$C(CH$_3$)$_2$NHCH$_2$CH(OH)CH$_3$ |
| NHSO$_2$N(CH$_3$)$_2$ | COCH$_2$C(CH$_3$)$_2$NHCH$_2$CH(OH)CH$_3$ |
| CN | COCH$_2$C(CH$_3$)$_2$NHCH$_2$CH(OH)CH$_2$OH |
| CONH$_2$ | COCH$_2$C(CH$_3$)$_2$NHCH$_2$CH(OH)CH$_2$OH |
| CH$_2$CONH$_2$ | COCH$_2$C(CH$_3$)$_2$NHCH$_2$CH(OH)CH$_2$OH |
| (CH$_2$)$_2$CONH$_2$ | COCH$_2$C(CH$_3$)$_2$NHCH$_2$CH(OH)CH$_2$OH |
| (CH$_2$)$_3$CONH$_2$ | COCH$_2$C(CH$_3$)$_2$NHCH$_2$CH(OH)CH$_2$OH |
| (CH$_2$)$_4$CONH$_2$ | COCH$_2$C(CH$_3$)$_2$NHCH$_2$CH(OH)CH$_2$OH |
| CONHC$_2$H$_5$ | COCH$_2$C(CH$_3$)$_2$NHCH$_2$CH(OH)CH$_2$OH |
| CONH(CH$_2$)$_3$OH | COCH$_2$C(CH$_3$)$_2$NHCH$_2$CH(OH)CH$_2$OH |
| CONH(CH$_2$)$_4$OH | COCH$_2$C(CH$_3$)$_2$NHCH$_2$CH(OH)CH$_2$OH |
| CN$_4$H | COCH$_2$C(CH$_3$)$_2$NHCH$_2$CH(OH)CH$_2$OH |
| CH$_2$CN$_4$H | COCH$_2$C(CH$_3$)$_2$NHCH$_2$CH(OH)CH$_2$OH |
| (CH$_2$)$_2$CN$_4$H | COCH$_2$C(CH$_3$)$_2$NHCH$_2$CH(OH)CH$_2$OH |
| (CH$_2$)$_3$CN$_4$H | COCH$_2$C(CH$_3$)$_2$NHCH$_2$CH(OH)CH$_2$OH |
| (CH$_2$)$_4$CN$_4$H | COCH$_2$C(CH$_3$)$_2$NHCH$_2$CH(OH)CH$_2$OH |
| CH$_2$NHCOCH$_3$ | COCH$_2$C(CH$_3$)$_2$NHCH$_2$CH(OH)CH$_2$OH |
| CH$_2$NHCONH$_2$ | COCH$_2$C(CH$_3$)$_2$NHCH$_2$CH(OH)CH$_2$OH |
| CH$_2$NHCONHCH$_3$ | COCH$_2$C(CH$_3$)$_2$NHCH$_2$CH(OH)CH$_2$OH |
| CH$_2$NHCON(CH$_3$)$_2$ | COCH$_2$C(CH$_3$)$_2$NHCH$_2$CH(OH)CH$_2$OH |
| CH$_2$NHCONHC$_2$H$_5$ | COCH$_2$C(CH$_3$)$_2$NHCH$_2$CH(OH)CH$_2$OH |
| CH$_2$NHCONH(CH$_2$)$_2$CH$_3$ | COCH$_2$C(CH$_3$)$_2$NHCH$_2$CH(OH)CH$_2$OH |
| CH$_2$NHCONH(CH$_2$)$_2$OH | COCH$_2$C(CH$_3$)$_2$NHCH$_2$CH(OH)CH$_2$OH |
| NHCONH$_2$ | COCH$_2$C(CH$_3$)$_2$NHCH$_2$CH(OH)CH$_2$OH |
| NHCONHCH$_3$ | COCH$_2$C(CH$_3$)$_2$NHCH$_2$CH(OH)CH$_2$OH |
| NHCONH(CH$_2$)$_2$OH | COCH$_2$C(CH$_3$)$_2$NHCH$_2$CH(OH)CH$_2$OH |
| NHSO$_2$NH$_2$ | COCH$_2$C(CH$_3$)$_2$NHCH$_2$CH(OH)CH$_2$OH |
| NHSO$_2$NHCH$_3$ | COCH$_2$C(CH$_3$)$_2$NHCH$_2$CH(OH)CH$_2$OH |
| NHSO$_2$N(CH$_3$)$_2$ | COCH$_2$C(CH$_3$)$_2$NHCH$_2$CH(OH)CH$_2$OH |
| NHSO$_2$N(C$_2$H$_5$)$_2$ | COCH$_2$C(CH$_3$)$_2$NHCH$_2$CH(OH)CH$_2$OH |

What is claimed is:

1. A compound which has the structure

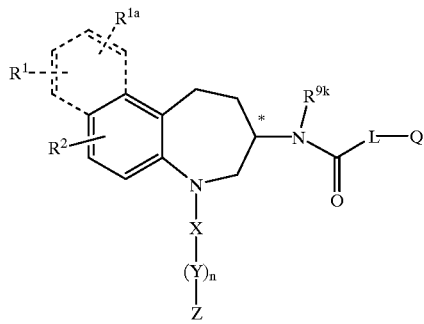

including a pharmaceutically acceptable salt thereof and all stereoisomers thereof,
wherein
X is $(CH_2)_m$ (wherein m is an integer from 0 to 4), SO or $SO_2$;

Y is

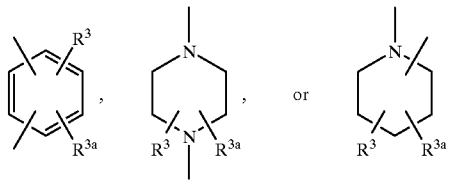

Z is

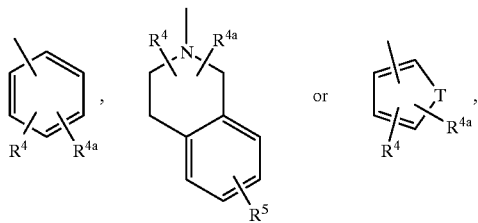

T is N—$R^6$, O or S;
provided that (1) where Y is

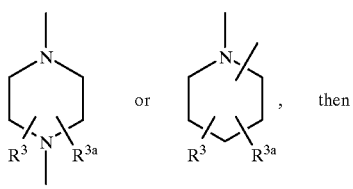

then

X is SO or $SO_2$ or $(CH_2)_m$ where m is 2, 3 or 4 and (2) where Z is

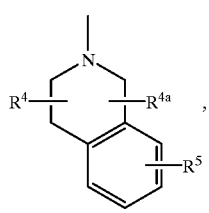

then n=o and X is SO or $SO_2$ or $(CH_2)_m$ where m is 2, 3 or 4;

L is

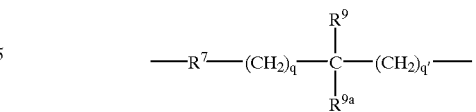

Q is —$NR^{10}R^{11}$,

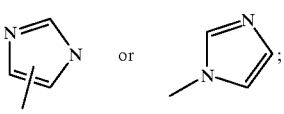

n is 0 to 1; q is 0 to 3; q' is 0 to 3;

the benzene ring depicted by broken lines may or may not be fused to the benzo ring of the benzoazepine;

$R^1$, $R^{1a}$, $R^2$, $R^3$ and $R^4$ are independently selected from hydrogen, hydroxy, halogen, cyano, nitro, amino, $CF_3$, $OCF_3$, $S(O)_rR^{9b}$, $SO_2NR^{9b}R^{9c}$, $COOR^{9b}$, $CONR^{9b}R^{9c}$, $NR^{9b}COR^{9c}$, alkyl, cycloalkyl, alkoxyl, alkylaryl, acyl, aryl or heteroaryl, and where the alkyl, cycloalkyl, alkoxyl, alkylaryl, acyl, aryl and heteroaryl groups in $R^1$, $R^{1a}$, $R^2$, $R^3$ and $R^4$ are optionally substituted with 1, 2 or 3 of hydroxy, halogen, cyano, nitro, amino, $CF_3$, $OCF_3$, $S(O)_rR^{9b}$, $SO_2NR^{9b}R^{9c}$, $CO_2R^{9b}$ and $CONR^{9b}R^{9c}$;

r is 0, 1 or 2;

$R^{3a}$, $R^{4a}$ and $R^5$ are independently selected from hydrogen, hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, $NHSO_2N(CH_3)_2$, tetrazole, —$R^{12}$alkyl, acyl, alkoxyl, alkylaryl, aryl or heteroaryl;

$R^{12}$ is selected from a bond, oxygen, $CONR^{9d}$, $S(O)_r$, $SO_2NR^{9d}$, $NR^{9d}$, $NR^{9d}CO$, $NR^{9d}CONR^{9e}$, and $NR^{9d}SO_2$, and where alkyl, acyl, alkoxyl, alkylaryl, aryl and heteroaryl groups in $R^{3a}$, $R^{4a}$ and $R^5$ are optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_rR^{9f}$, $SO_2NR^{9f}R^{9g}$ or tetrazole;

t and t' are independently 0, 1 or 2;

$R^6$ is selected from hydrogen, $SO_2R^{9h}$, $SO_2NR^{9h}R^{9i}$, $CONR^{9h}R^{9i}$, alkyl, cycloalkyl, acyl or aryl, where the alkyl, cycloalkyl, acyl or aryl groups in $R^6$ is optionally substituted with 1, 2 or 3 of hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, or tetrazole;

$R^7$ is selected from a bond, oxygen or $NR^{9j}$;

$R^9$ and $R^{9a}$ are independently selected from hydrogen, $CF_3$, alkyl or alkylaryl, or $R^9$ and $R^{9a}$ can be joined together to form a 4 to 7 membered carbocyclic or heterocyclic ring, or either $R^9$ or $R^{9a}$, or both, can be joined with $R^{10}$ or $R^{11}$ to form a 4 to 7 membered heterocyclic ring; and $R^9$ and $R^{9a}$ can be optionally substituted with any of the substituents for $R^6$;

$R^{9b}$, $R^{9c}$, $R^{9d}$, $R^{9e}$, $R^{9f}$, $R^{9g}$, $R^{9h}$, $R^{9i}$, $R^{9j}$ and $R^{9k}$ are independently selected from hydrogen, alkyl or aryl;

$R^{10}$ and $R^{11}$ are independently selected from hydrogen, alkyl or alkylaryl, and where the alkyl and alkylaryl groups in $R^{10}$ and $R^{11}$ can be optionally substituted with 1 to 3 of hydroxy, amino, alkoxyl, aryloxyl, acyl and imidazole; or $R^{10}$ and $R^{11}$ can be joined together to form a 4 to 7 membered heterocyclic ring.

2. A compound which has the structure

[chemical structure diagram]

including a pharmaceutically acceptable salt thereof and all stereoisomers thereof, wherein X is CO;

Y is

[three chemical structure diagrams with $R^3$, $R^{3a}$ substituents]

Z is

[three chemical structure diagrams with $R^4$, $R^{4a}$, $R^5$, T substituents]

T is N—$R^6$, O or S;

provided that where Z is

[chemical structure diagram]

then n=o;

L is ——$R^7$——$(CH_2)_q$——aryl——$(CH_2)_{q'}$—— or

——$R^7$——$(CH_2)_q$——$\overset{R^9}{\underset{R^{9a}}{C}}$——$(CH_2)_{q'}$——

Q is ——$NR^{10}R^{11}$,

[two imidazole structures] or ;

n is 0 to 1; q is 0 to 3; q' is 0 to 3;

the benzene ring depicted by broken lines may or may not be fused to the benzo ring of the benzoazepine;

$R^1$, $R^{1a}$, $R^2$, $R^3$ and $R^4$ are independently selected from hydrogen, hydroxy, halogen, cyano, nitro, $CF_3$, $OCF_3$, $S(O)_rR^{9b}$, $SO_2NR^{9b}R^{9c}$, $COOR^{9b}$, alkyl, cycloalkyl, alkoxyl, alkylaryl, acyl, aryl or heteroaryl, and where the alkyl, cycloalkyl, alkoxyl, alkylaryl, acyl, aryl and heteroaryl groups in $R^1$, $R^{1a}$, $R^2$, $R^3$ and $R^4$ are optionally substituted with 1, 2 or 3 of hydroxy, halogen, cyano, nitro, amino, $CF_3$, $OCF_3$, $S(O)_rR^{9b}$, $SO_2NR^{9b}R^{9c}$, $CO_2R^{9b}$ and $CONR^{9b}R^{9c}$;

r is 0, 1 or 2;

$R^{3a}$, $R^{4a}$ and $R^5$ are independently selected from hydrogen, hydroxy, halogen, cyano, nitro, $CF_3$, $OCF_3$, $CO_2H$, $SO_2NH_2$, $SO_2CH_3$, $NHSO_2CH_3$, $NHSO_2N(CH_3)_2$, tetrazole, —$R^{12}$alkyl, acyl, alkoxyl, alkylaryl, aryl or heteroaryl;

$R^{12}$ is selected from a bond, oxygen, $CONR^{9d}$, $S(O)_t$, $SO_2NR^{9d}$, $NR^{9d}$, $NR^{9d}CO$, $NR^{9d}CONR^{9e}$, and $NR^{9d}SO_2$, and where alkyl, acyl, alkoxyl, alkylaryl, aryl and heteroaryl groups in $R^{3a}$, $R^{4a}$ and $R^5$ are optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_{t'}R^{9f}$, $SO_2NR^{9f}R^{9g}$ or tetrazole;

t and t' are independently 0, 1 or 2;

$R^6$ is selected from hydrogen, $SO_2R^{9h}$, $SO_2NR^{9h}R^{9i}$, $CONR^{9h}R^{9i}$, alkyl, cycloalkyl, acyl or aryl, where the alkyl, cycloalkyl, acyl or aryl groups in $R^6$ is optionally substituted with 1, 2 or 3 of hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, or tetrazole;

$R^7$ is selected from a bond, oxygen or $NR^{9j}$;

$R^9$ and $R^{9a}$ are independently selected from hydrogen, $CF_3$, alkyl or alkylaryl, or $R^9$ and $R^{9a}$ can be joined together to form a 4 to 7 membered carbocyclic or heterocyclic ring, or either $R^9$ or $R^{9a}$, or both, can be joined with $R^{10}$ or $R^{11}$ to form a 4 to 7 membered heterocyclic ring; and $R^9$ and $R^{9a}$ can be optionally substituted with any of the substituents for $R^6$;

$R^{9b}$, $R^{9c}$, $R^{9d}$, $R^{9e}$, $R^{9f}$, $R^{9g}$, $R^{9h}$, $R^{9i}$, $R^{9j}$ and $R^{9k}$ are independently selected from hydrogen, alkyl or aryl;

$R^{10}$ and $R^{11}$ are independently selected from hydrogen, alkyl or alkylaryl, and where the alkyl and alkylaryl groups in $R^{10}$ and $R^{11}$ can be optionally substituted with 1 to 3 of hydroxy, amino, alkoxyl, aryloxyl, acyl and imidazole; or $R^{10}$ and $R^{11}$ can be joined together to form a 4 to 7 membered heterocyclic ring.

3. A compound which has the structure

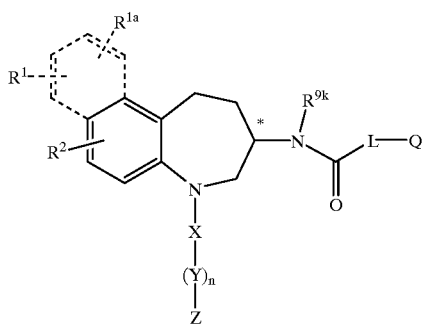

including a pharmaceutically acceptable salt thereof and all stereoisomers thereof, wherein X is CO;

Y is

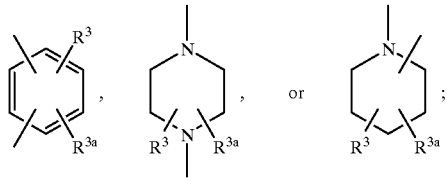

Z is

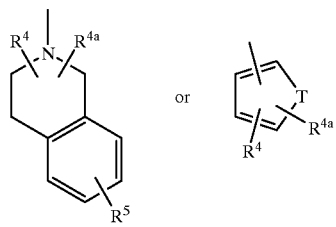

T is N—$R^6$, O or S;

provided that where Z is

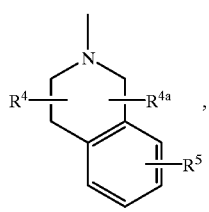

then n=o;

L is

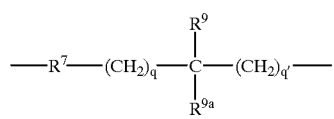

Q is —$NR^{10}R^{11}$,

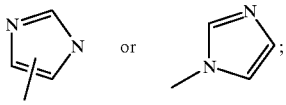

n is 0 to 1; q is 0 to 3; q' is 0 to 3;

the benzene ring depicted by broken lines may or may not be fused to the benzo ring of the benzoazepine;

$R^1$, $R^{1a}$, $R^2$, $R^3$ and $R^4$ are independently selected from hydrogen, hydroxy, halogen, cyano, nitro, amino, $CF_3$, $OCF_3$, $S(O)_rR^{9b}$, $SO_2NR^{9b}R^{9c}$, $COOR^{9b}$, $CONR^{9b}R^{9c}$, $NR^{9b}COR^{9c}$, alkyl, cycloalkyl, alkoxyl, alkylaryl, acyl, aryl or heteroaryl, and where the alkyl, cycloalkyl, alkoxyl, alkylaryl, acyl, aryl and heteroaryl groups in $R^1$, $R^{1a}$, $R^2$, $R^3$ and $R^4$ are optionally substituted with 1, 2 or 3 of hydroxy, halogen, cyano, nitro, amino, $CF_3$, $OCF_3$, $S(O)_rR^{9b}$, $SO_2NR^{9b}R^{9c}$, $CO_2R^{9b}$ and $CONR^{9b}R^{9c}$;

r is 0, 1 or 2;

$R^{3a}$, $R^{4a}$ and $R^5$ are independently selected from hydrogen, hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, $NHSO_2N(CH_3)_2$, tetrazole —$R^{12}$alkyl, acyl, alkoxyl, alkylaryl, aryl or heteroaryl;

$R^{12}$ is selected from a bond, oxygen, $CONR^{9d}$, $S(O)_r$, $SO_2NR^{9d}$, $NR^{9d}$, $NR^{9d}CO$, $NR^{9d}CONR^{9e}$, and $NR^{9d}SO_2$, and where alkyl, acyl, alkoxyl, alkylaryl, aryl and heteroaryl groups in $R^{3a}$, $R^{4a}$ and $R^5$ are optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_rR^{9f}$, $SO_2NR^{9f}R^{9g}$ or tetrazole;

t and t' are independently 0, 1 or 2;

$R^6$ is selected from hydrogen, $SO_2R^{9h}$, $SO_2NR^{9h}R^{9i}$, $CONR^{9h}R^{9i}$, alkyl, cycloalkyl, acyl or aryl, where the alkyl, cycloalkyl, acyl or aryl groups in $R^6$ is optionally substituted with 1, 2 or 3 of hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, or tetrazole;

$R^7$ is selected from a bond, oxygen or $NR^{9j}$;

$R^9$ and $R^{9a}$ are independently selected from hydrogen, $CF_3$, alkyl or alkylaryl, or $R^9$ and $R^{9a}$ can be joined together to form a 4 to 7 membered carbocyclic or heterocyclic ring, or either $R^9$ or $R^{9a}$, or both, can be joined with $R^{10}$ or $R^{11}$ to form a 4 to 7 membered heterocyclic ring; and $R^9$ and $R^{9a}$ can be optionally substituted with any of the substituents for $R^6$;

$R^{9b}$, $R^{9c}$, $R^{9d}$, $R^{9e}$, $R^{9f}$, $R^{9g}$, $R^{9h}$, $R^{9i}$, $R^{9j}$ and $R^{9k}$ are independently selected from hydrogen, alkyl or aryl;

$R^{10}$ and $R^{11}$ are independently selected from hydrogen, alkyl or alkylaryl, and where the alkyl and alkylaryl groups in $R^{10}$ and $R^{11}$ can be optionally substituted with 1 to 3 of hydroxy, amino, alkoxyl, aryloxyl, acyl and imidazole; or $R^{10}$ and $R^{11}$ can be joined together to form a 4 to 7 membered heterocyclic ring.

4. The compound as defined in claim 1 having the structure

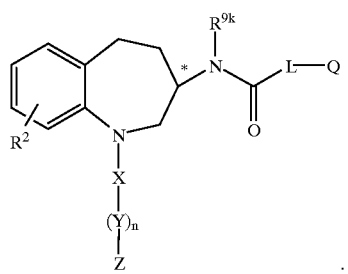

5. The compound as defined in claim 1 having the structure

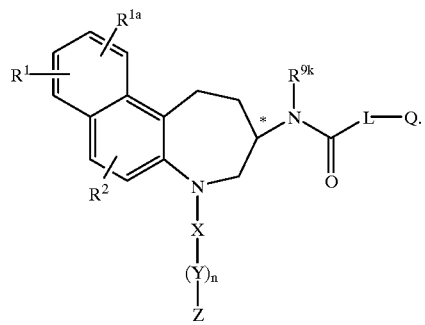

6. The compound as defined in claim 1 wherein X is $(CH_2)_m$.

7. The compound as defined in claim 1 wherein Y is

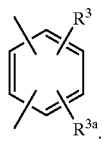

8. The compound as defined in claim 1 wherein Z is

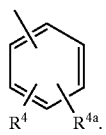

9. The compound as defined in claim 1 wherein $-(Y)_n-Z$ is

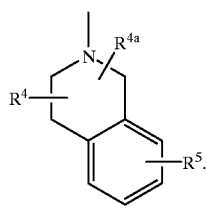

10. The compound as defined in claim 6 wherein X is $CH_2$.

11. The compound as defined in claim 7 wherein Y is

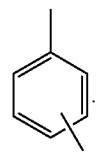

12. The compound as defined in claim 8 wherein Z is

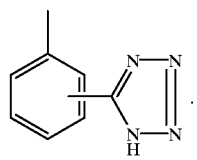

13. The compound as defined in claim 1 wherein

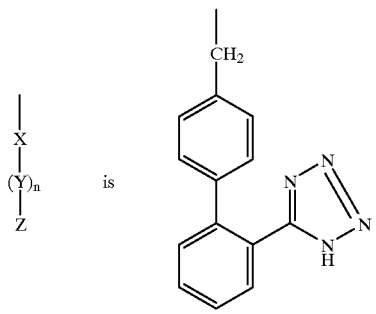

is

14. The compound as defined in claim 1 having the structure

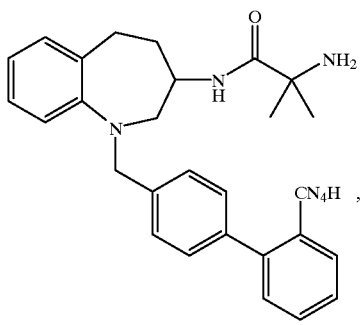

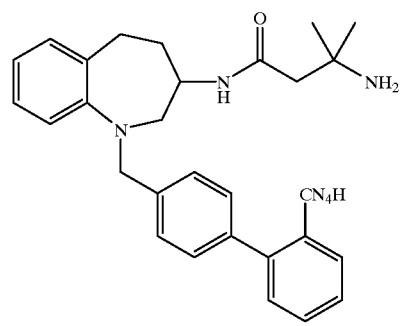

or

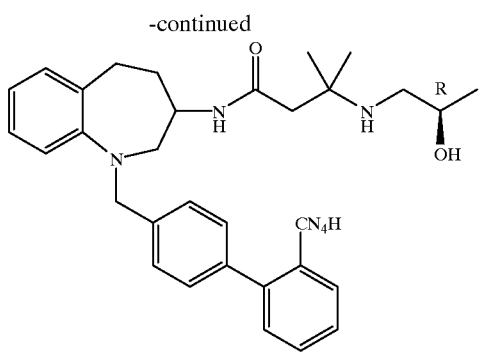

15. A pharmaceutical composition comprising a compound as defined in claim 1 and a pharmaceutically acceptable carrier therefor.

16. A pharmaceutical composition comprising at least one compound of claim 2 and a pharmaceutically acceptable carrier therefor.

17. A pharmaceutical composition comprising at least one compound of claim 3 and a pharmaceutically acceptable carrier therefor.

18. A method for increasing levels of endogenous growth hormone, which comprises administering to a patient in need of treatment a therapeutically effective amount of at least one compound of the formula

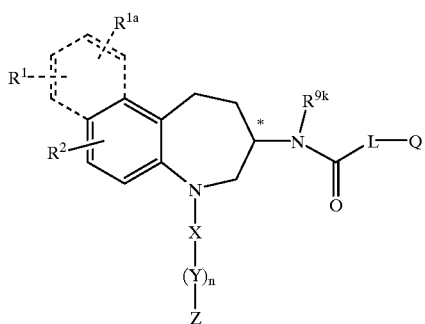

including a pharmaceutically acceptable salt thereof and all stereoisomers thereof, wherein X is $(CH_2)_m$ (wherein m is an integer from 0 to 4), CO, SO or $SO_2$;

Y is

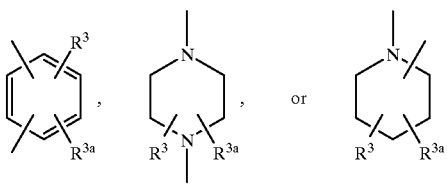

Z is

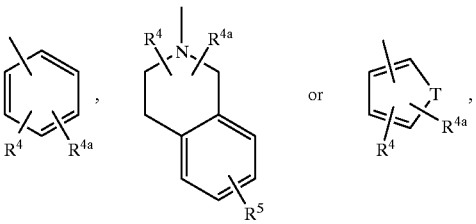

T is N—$R^6$, O or S;
provided that (1) where Y is

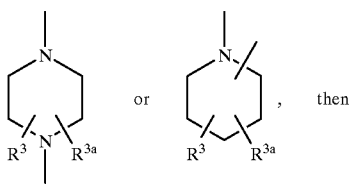

X is CO, SO or $SO_2$ or $(CH_2)_m$ where m is 2, 3 or 4 and (2) where Z is

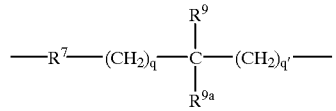

then n=o and X is CO, SO or $SO_2$ or $(CH_2)_m$ where m is 2, 3 or 4;

L is 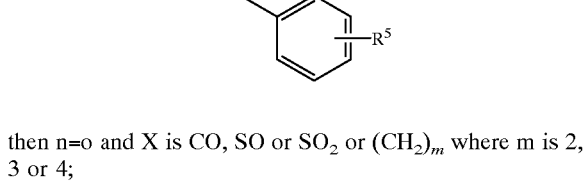

Q is —$NR^{10}R^{11}$,

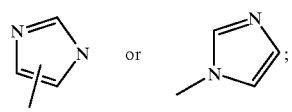

n is 0 to 1; q is 0 to 3; q' is 0 to 3;
the benzene ring depicted by broken lines may or may not be fused to the benzo ring of the benzoazepine;
$R^1$, $R^{1a}$, $R^2$, $R^3$ and $R^4$ are independently selected from hydrogen, hydroxy, halogen, cyano, nitro, amino, $CF_3$, $OCF_3$, $S(O)_rR^{9b}$, $SO_2NR^{9b}R^{9c}$, $COOR^{9b}$, $CONR^{9b}R^{9c}$; $NR^{9b}COR^{9c}$, alkyl, cycloalkyl, alkoxyl, alkylaryl, acyl, aryl or heteroaryl, and where the alkyl, cycloalkyl, alkoxyl, alkylaryl, acyl, aryl and heteroaryl groups in $R^1$, $R^{1a}$, $R^2$, $R^3$ and $R^4$ are optionally substituted with 1, 2 or 3 of hydroxy, halogen, cyano, nitro, amino, $CF_3$, $OCF_3$, $S(O)_rR^{9b}$, $SO_2NR^{9b}R^{9c}$, $CO_2R^{9b}$ and $CONR^{9b}R^{9c}$;
r is 0, 1 or 2;

$R^{3a}$, $R^{4a}$ and $R^5$ are independently selected from hydrogen, hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, $NHSO_2N(CH_3)_2$, tetrazole, —$R^{12}$alkyl, acyl, alkoxyl, alkylaryl, aryl or heteroaryl;

$R^{12}$ is selected from a bond, oxygen, $CONR^{9d}$, $S(O)_t$, $SO_2NR^{9d}$, $NR^{9d}$, $NR^{9d}CO$, $NR^{9d}CONR^{9e}$, and $NR^{9d}SO_2$, and where alkyl, acyl, alkoxyl, alkylaryl, aryl and heteroaryl groups in $R^{3a}$, $R^{4a}$ and $R^5$ are optionally substituted with 1, 2 or 3 of halogen, cyano, $CF_3$, $OCF_3$, $OR^{9f}$, $NR^{9f}R^{9g}$, $COOR^{9f}$, $COR^{9f}$, $CONR^{9f}R^{9g}$, $S(O)_tR^{9f}$, $SO_2NR^{9f}R^{9g}$ or tetrazole;

t and t' are independently 0, 1 or 2;

$R^6$ is selected from hydrogen, $SO_2R^{9h}$, $SO_2NR^{9h}R^{9i}$, $CONR^{9h}R^{9i}$, alkyl, cycloalkyl, acyl or aryl, where the alkyl, cycloalkyl, acyl or aryl groups in $R^6$ is optionally substituted with 1, 2 or 3 of hydroxy, halogen, cyano, nitro, amino, $CF_3$, $OCF_3$, $CO_2H$, $CONH_2$, $SO_2NH_2$, $SO_2CH_3$, $NHCON(CH_3)_2$, $NHSO_2CH_3$, or tetrazole;

$R^7$ is selected from a bond, oxygen or $NR^{9j}$;

$R^9$ and $R^{9a}$ are independently selected from hydrogen, $CF_3$, alkyl or alkylaryl, or $R^9$ and $R^{9a}$ can be joined together to form a 4 to 7 membered carbocyclic or heterocyclic ring, or either $R^9$ or $R^{9a}$, or both, can be joined with $R^{10}$ or $R^{11}$ to form a 4 to 7 membered heterocyclic ring; and $R^9$ and $R^{9a}$ can be optionally substituted with any of the substituents for $R^6$;

$R^{9b}$, $R^{9c}$, $R^{9d}$, $R^{9e}$, $R^{9f}$, $R^{9g}$, $R^{9h}$, $R^{9i}$, $R^{9j}$ and $R^{9k}$ are independently selected from hydrogen, alkyl or aryl;

$R^{10}$ and $R^{11}$ are independently selected from hydrogen, alkyl or alkylaryl, and where the alkyl and alkylaryl groups in $R^{10}$ and $R^{11}$ can be optionally substituted with 1 to 3 of hydroxy, amino, alkoxyl, aryloxyl, acyl and imidazole; or $R^{10}$ and $R^{11}$ can be joined together to form a 4 to 7 membered heterocyclic ring.

19. A method for treating obesity, osteoporosis, renal disease, cardiac myopathy, cachexia, HIV wasting syndrome, long term critical illness, sarcopenia, and/or stimulating wound healing and/or the immune system, or increasing muscle mass and/or strength, which comprises administering to a patient in need of treatment a therapeutically effective amount of a compound as defined in claim 18.

20. A method for the increased production of wool, milk, and meat by treating animals with a therapeutically effective amount of a compound as defined in claim 18.

21. A method for treating Syndrome X, which comprises administering to a patient in need of treatment a therapeutically effective amount of a compound as defined in claim 18.

22. A method for treating diabetes and/or increasing lean body mass, which comprises administering to a patient in need of treatment a therapeutically effective amount of at least one compound as defined in claim 18.

* * * * *